United States Patent
Mittelstein et al.

(10) Patent No.: US 6,506,176 B1
(45) Date of Patent: Jan. 14, 2003

(54) METHODS, APPARATUS AND SYSTEM FOR REMOVAL OF LENSES FROM MAMMALIAN EYES

(75) Inventors: Michael Mittelstein, Laguna Niguel, CA (US); John T. Sorensen, Aliso Viejo, CA (US); Soheila Mirhashemi, Laguna Niguel, CA (US); James B. Gerg, Lake Forest, CA (US); John I. Muri, Aliso Viejo, CA (US); Roger F. Etherington, Newport Beach, CA (US); John A. Ripley, Newport Beach, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/505,098

(22) Filed: Feb. 16, 2000

Related U.S. Application Data

(60) Provisional application No. 60/120,538, filed on Feb. 17, 1999.

(51) Int. Cl.[7] .................................................. A61F 9/00
(52) U.S. Cl. ..................... 604/22; 604/107; 604/170; 604/180
(58) Field of Search ............................. 604/22; 606/107, 606/170, 180

(56) References Cited

U.S. PATENT DOCUMENTS

| | | | |
|---|---|---|---|
| 3,732,858 A | 5/1973 | Banko | |
| 3,818,913 A | 6/1974 | Wallach | |
| 3,937,222 A | * 2/1976 | Banko | 606/170 |
| 3,976,077 A | 8/1976 | Kerfoot, Jr. | |
| 4,002,169 A | 1/1977 | Cupler, II | |
| 4,061,146 A | 12/1977 | Baehr et al. | |
| 4,167,944 A | 9/1979 | Banko | |
| 4,289,131 A | 9/1981 | Mueller | |
| 4,320,761 A | 3/1982 | Haddad | |
| 4,368,734 A | 1/1983 | Banko | |
| 4,445,509 A | 5/1984 | Auth | |
| 4,631,052 A | 12/1986 | Kensey | |
| 4,646,736 A | 3/1987 | Auth | |
| 4,649,919 A | 3/1987 | Thimsen et al. | |
| 4,681,106 A | 7/1987 | Kensey et al. | |
| 4,700,705 A | 10/1987 | Kensey et al. | |
| 4,747,821 A | 5/1988 | Kensey et al. | |
| 4,770,174 A | 9/1988 | Luckman et al. | |
| 4,811,735 A | 3/1989 | Nash et al. | |
| 4,823,793 A | 4/1989 | Angulo et al. | |
| 4,825,865 A | 5/1989 | Zelman | |
| 4,908,015 A | 3/1990 | Anis | |

(List continued on next page.)

FOREIGN PATENT DOCUMENTS

| | | |
|---|---|---|
| DE | 3801318 | 7/1989 |
| EP | 0147192 | 7/1985 |
| EP | 0310685 | 4/1989 |
| EP | 0286415 | 10/1998 |
| GB | 2239060 | 6/1991 |
| WO | WO08900834 | 2/1989 |
| WO | WO8906517 | 7/1989 |
| WO | WO9211816 | 7/1992 |

*Primary Examiner*—J. Casimer Jacyna
(74) *Attorney, Agent, or Firm*—Michael L. Smith

(57) ABSTRACT

A system for removing the lens from an eye of a mammal, including a lens-removal device having a probe for penetrating the lens capsule. The probe includes a sheath that shields a rotating impeller at all times, with the impeller being pneumatically actuated to advance to a lens removal position within the sheath. The impeller is pneumatically rotated using a turbine mechanism within a handle for the probe. Irrigation and aspiration are provided to facilitate removal of the lens tissue. The turbine is driven with pulsed air to prevent stiction. A purge/protection cap helps remove air bubbles from the system prior to use and protects the delicate impeller during transport. An operating system is also provided with a foot pedal actuator.

43 Claims, 11 Drawing Sheets

U.S. PATENT DOCUMENTS

| | | |
|---|---|---|
| 5,057,098 A | 10/1991 | Zelman |
| 5,074,867 A | 12/1991 | Wilk |
| 5,123,904 A | 6/1992 | Shimomura et al. |
| 5,133,729 A | 7/1992 | Sjostrom |
| 5,154,969 A | 10/1992 | Kerawalla |
| 5,222,959 A | 6/1993 | Anis |
| 5,437,678 A | 8/1995 | Sorensen .................... 606/107 |
| 5,492,528 A | 2/1996 | Anis |
| 5,690,641 A | 11/1997 | Sorensen et al. ............ 606/107 |
| 5,693,062 A | 12/1997 | Stegmann et al. |
| 5,733,297 A * | 3/1998 | Wang .......................... 606/170 |
| 5,782,795 A * | 7/1998 | Bays ............................ 604/22 |
| 5,807,401 A * | 9/1998 | Grieshaber et al. ......... 606/107 |
| 6,007,513 A * | 12/1999 | Anis et al. .................... 604/22 |
| 6,142,996 A | 11/2000 | Mirhashemi et al. |

* cited by examiner

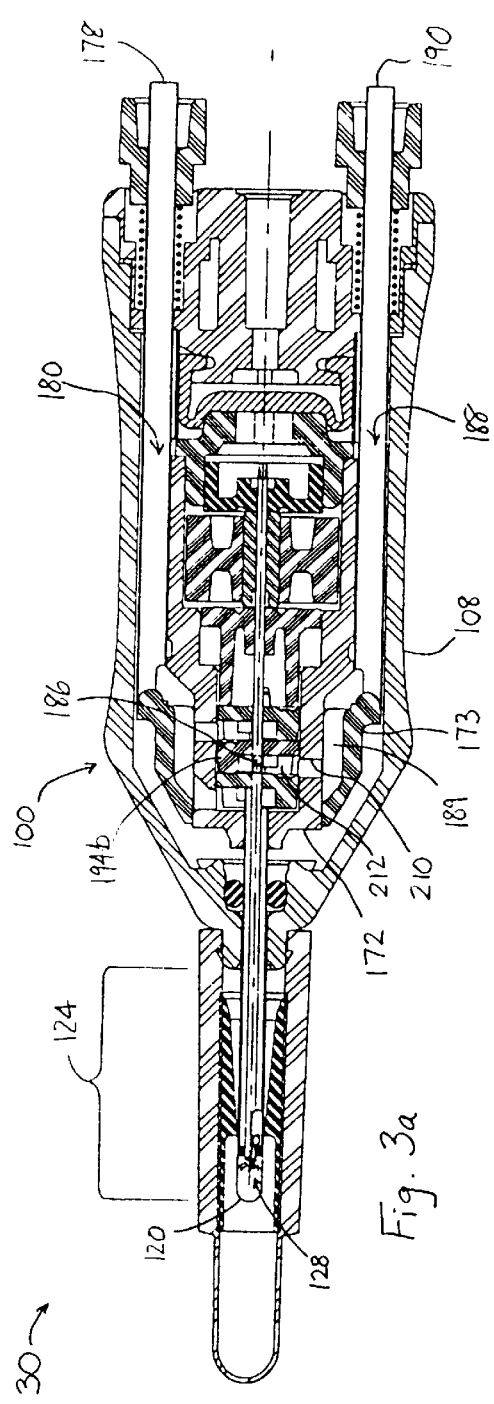
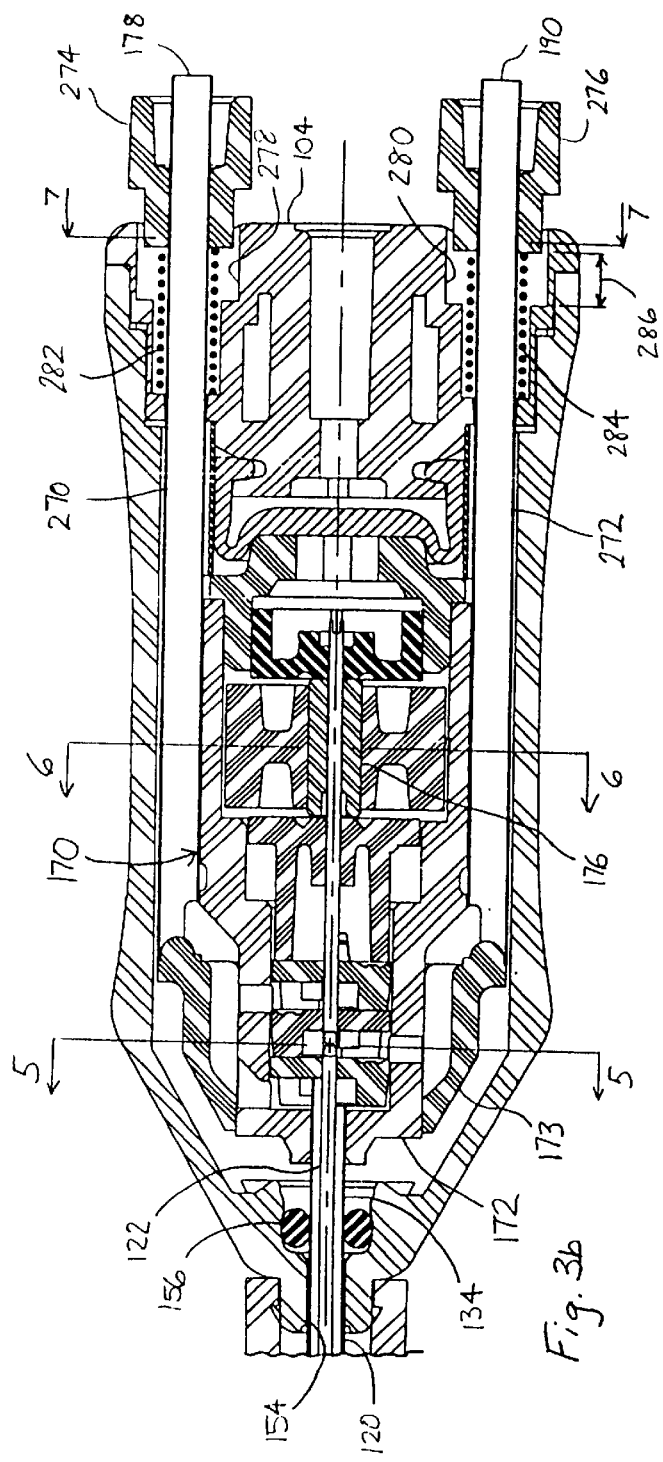
Fig. 3a
Fig. 3b

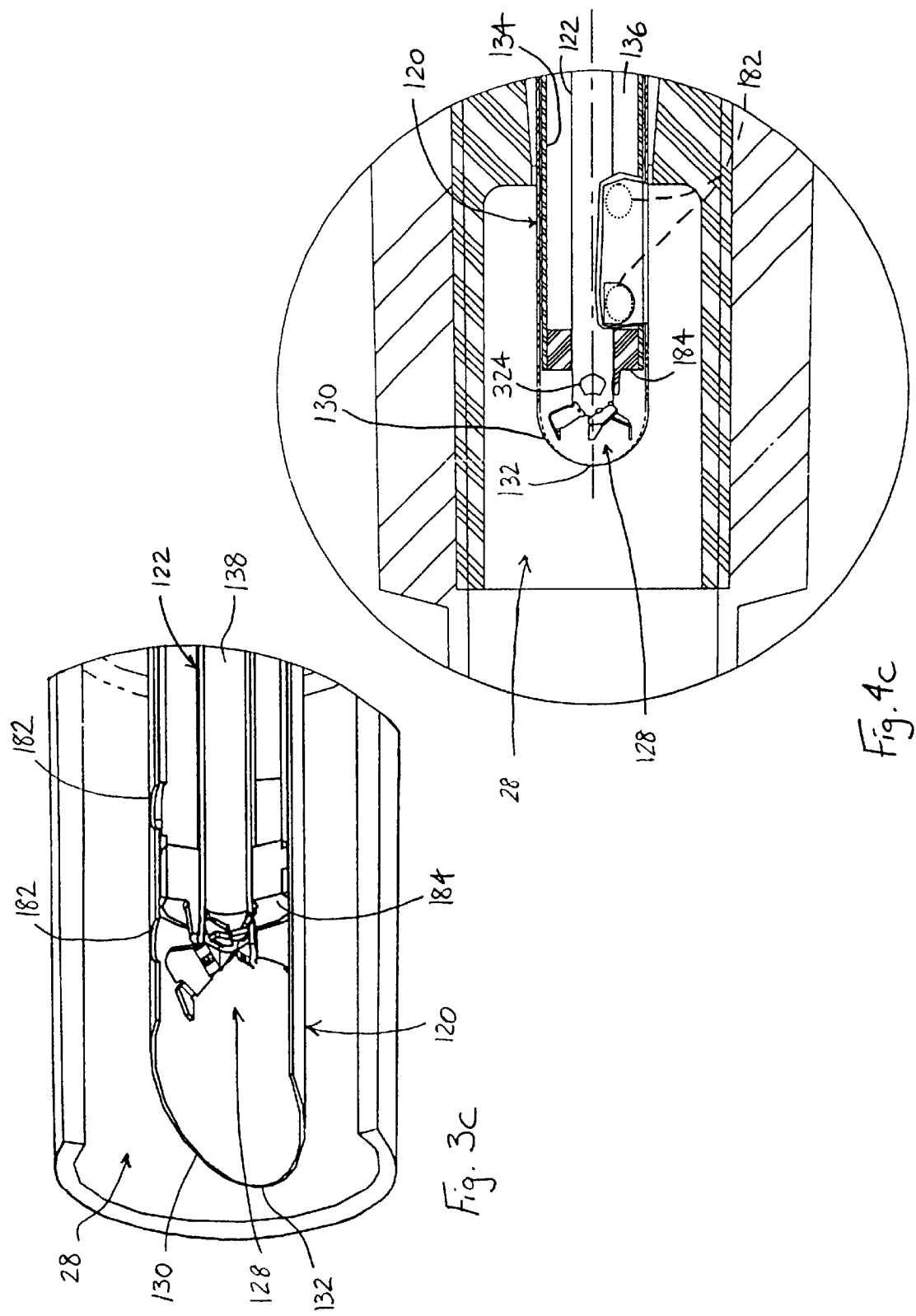

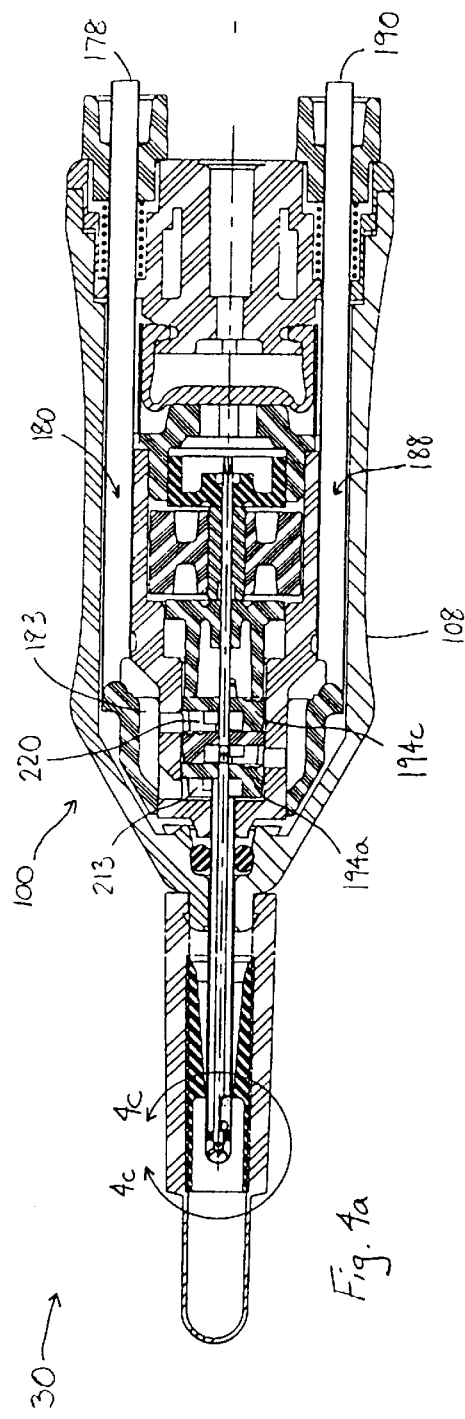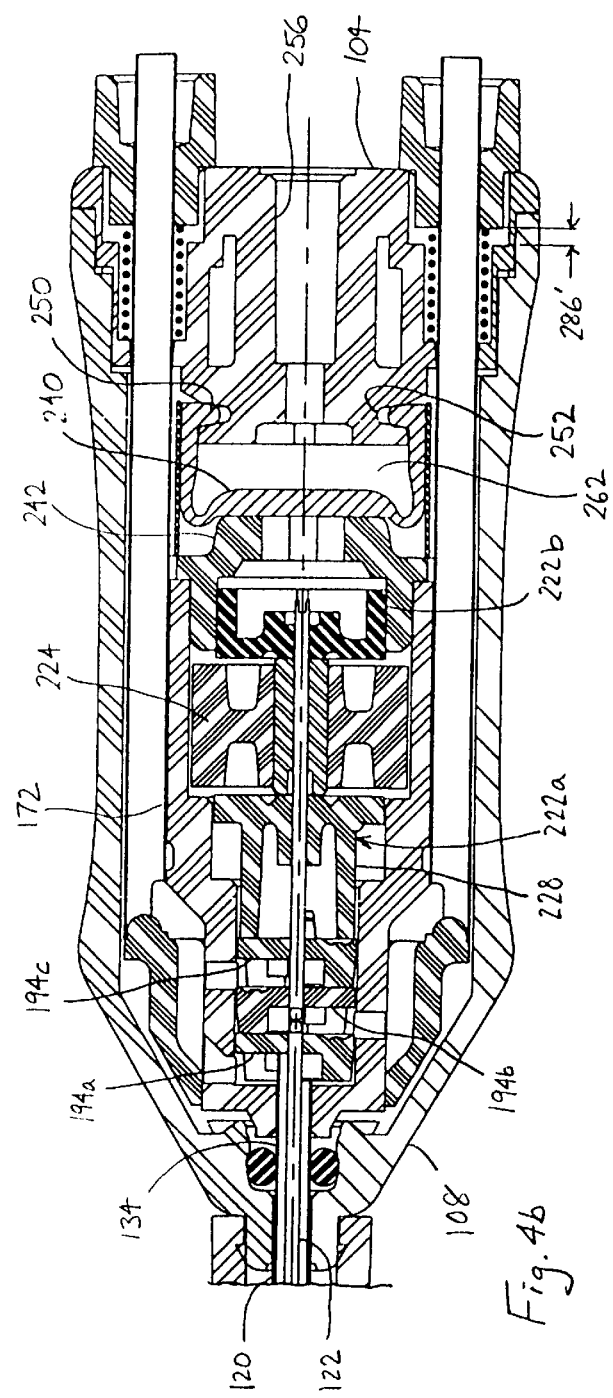

METHODS, APPARATUS AND SYSTEM FOR REMOVAL OF LENSES FROM MAMMALIAN EYES

RELATED APPLICATION

This patent application claims priority to U.S. Provisional Patent Application Serial No. 60/120,538 filed on Feb. 17, 1999, entitled Method, Apparatus and System for Removing Cataract-Affected Lenses From Mammalian Eyes.

FIELD OF THE INVENTION

This invention relates generally to medical methods and devices, and more particularly to methods and devices for removing the lenses from the eyes of mammalian patients.

BACKGROUND OF THE INVENTION

A. Pathological and Age Related Changes of the Ophthalmic Lens

The lens of a human eye is a crystalline, transparent biconvex structure that serves to focus rays of light on the retina of the eye. The lens consists of a central portion or "nucleus" and a peripheral portion or "cortex" and is enclosed within a lens capsule. The lens capsule is a bag-like anatomical structure that surrounds the lens and is suspended by fine ligaments that are attached to the ciliary muscles. The ciliary muscles radially stretch and relax the capsule thereby flexing the lens in a manner that varies the optical characteristics of the lens to provide the desired focus for an image. This is commonly referred to as accommodation.

The lens cortex is a jelly-like portion of the lens and is located between the denser inner nucleus and the elastic outer capsule. The lens nucleus is an optically defined-zone which is denser in the central position of the lens. The lens nucleus becomes even denser with age, and can eventually harden and fill increasing portions of the total lens space. Age-related hardening of the lens typically results in a condition known as presbyopia or farsightedness. Additionally the lens may become opacified and/or cloudy. This opacity or cloudiness of the lens is commonly referred to as a cataract.

B. The Pathogenesis and Treatment of Cataracts

Cataracts can be present at birth or can be caused by trauma, toxins, radiation, or certain diseases (e.g., diabetes mellitus). Approximately ninety percent of all cataracts form as a result of the aging of the lens, which can occur as early as age 40. Although cataracts can develop in people at any age, it is a virtual certainty that people who live long lives will eventually develop some degree of cataracts.

The cataractous lens obstructs the passage of light and tends to prevent the formation of a clear image on the retina. Once a cataract develops, it typically becomes more severe over a period of years, though some develop more rapidly. As a cataract "matures," the initial change is a yellowing in the lens, which becomes cloudy or opacified.

There is one stage in the development of some cataracts when "near" vision actually improves while "distance" vision worsens. This condition is known as "second sight," when some people can read without their glasses. However, the cataract will continue to progress so that even "near" vision becomes blurred.

Surgery (i.e., surgical removal of the cataractous lens) is currently the only method of restoring vision in a patient who suffers from cataracts. Generally, four types of surgical procedures are known to be useable for removing cataract-affected lenses. These four types of surgical procedures are, as follows:

Extracapsular Cataract Extraction (ECCE): An incision about 10 mm long is made in the lens capsule and the surgeon extracts the harder nucleus of the lens usually in one piece. The softer peripheral portions of the lens are then suctioned out. The typical ECCE procedure results in disruption or removal of a substantial portion of the anterior aspect of the lens capsule.

Intracapsular Cataract Extraction (ICCE): An incision about 15 mm long is made in the lens capsule and the surgeon extracts the whole lens, usually in one piece. The ICCE procedure results in disruption of the zonules so as to detach the lens with its capsule from the surrounding ciliary muscles. At least in the United States, ICCE is no longer a widely used method.

Phacoemulsification (PE): For the phacoemulsification procedure, a limbal or corneal incision of about 3 mm is made allowing insertion of the instrument's tip into the anterior chamber in a direction almost parallel to the iris. Once the incision has been made, the central part of the anterior lens capsule is typically opened widely to facilitate emulsification of the lens nucleus and cortical clean-up, as well as to provide for an ideal intraocular lens placement into the capsule.

When compared to conventional extracapsular cataract removal procedures, the phacoemulsification technique provides the advantages of a smaller incision, a stronger post-operative globe which reduces astigmatism, better wound closure, lower trauma and quicker improvement in vision. However, this phacoemulsification procedure is contraindicated, except with respect to the most highly skilled surgeon, in patients having a dislocated cataract lens, a shallow anterior chamber, miotic pupils, or low cornea-endothelial cell counts.

Inadvertent perforation of the posterior aspect of the lens capsule during the phacoemulsification procedure can result in vitreous prolapse into the lens capsule. Also, stray ultrasound energy from the phacoemulsification procedure can be destructive to the endothelial cells of the cornea, and can ultimately result in complete degeneration of the cornea.

i. Endocapsular Phacoemulsification

In a rarely performed procedure, the cataractous lens is removed by an endocapsular phacoemulsification. The cataractous lens must be carved away while not only the posterior side of the lens capsule but also most of the anterior side are left intact. A significant amount of operator skill and training is required to perform endocapsular phacoemulsification. The operator must repeatedly move the ultrasound probe back and forth, while altering its angle, to effect complete emulsification of the lens without causing trauma to or inadvertently perforating the lens capsule.

ii. Extracapsular Phacoemulsification

Extracapsular phacoemulsification can be performed in the anterior chamber or posterior chamber of the eye. In the case of anterior chamber phacoemulsification, the cataract lens is maneuvered into the anterior chamber where it is carved and removed from the chamber. Anterior chamber phacoemulsification is more traumatic to the endothelial layer of the cornea than posterior chamber phacoemulsification, but it is often an easier procedure for the surgeon to perform. Posterior chamber phacoemulsification consists of carving or shaving the central part of the lens while the lens is still in the lens capsule. This method is more difficult to perform than ECCE due to the possibility of rupturing the posterior lens capsule and exposing the vitreous which fills the volume of the posterior eyeball.

EndocapsularVortex Emulsification (EVE): The procedure is described in applicants' prior U.S. Pat. No. 5,437,678 (Sorensen), U.S. Pat. No. 5,690,641. (Sorensen et al.) and U.S. Pat. No. 5,871,492 (Sorensen). In the procedure, an EVE probe having a rotating lens-reducing head is inserted into the lens capsule through a small opening of approximately 1–3 mm that is formed in the periphery of the lens capsule. The 1–3 mm opening in the lens capsule may be formed by an electrosurgical capsulotomy device of the type described in U.S. patent application Ser. No. 08/744, 404 (Mirhashemi, et al.) The EVE probe is held in a substantially stationary position while the lens-reducing head is rotated. Concurrently with the rotation of the lens-reducing head, an irrigation solution (e.g., balanced salt solution) is gently infused through the probe and excess irrigation solution and debris are aspirated out of the lens capsule causing the nucleus to rotate and thereby coming into contact with the lens reducing head. The flow causes the entire lens (including the relatively hard nucleus) to be repeatedly brought into contact with the rotating lens reducing head and fully emulsified, without the need for substantial movement or manipulation of the position of the probe. In this manner, the entire lens is removed through the small 1–3 mm opening and the anterior aspect of the lens capsule remains essentially intact.

In addition to the ECCE, PE and EVE devices and procedures described hereabove, several other devices and procedures have also been purported to be useable for removing cataract-affected lenses. These other devices and procedures include those described in U.S. Pat. No. 3,732,858 (Banko), U.S. Pat. No. 4,167,944 (Banko), U.S. Pat. No. 4,363,743 (Banko), and U.S. Pat. No. 4,646,736 (Auth).

C. The Pathogenesis of and Treatments for Presbyopia

As pointed out hereabove, the ability of the human eye to change focus depends upon the inherent elasticity of the lens. However, the human lens typically undergoes a gradual loss of elasticity and/or swells with the aging process, thereby causing a gradual decrease in the eye's ability to focus on objects that are close up. Clinically, this condition is known as presbyopia. Presbyopia occurs to some degree in almost everyone, during the aging process.

Presbyopia has heretofore been treated with prescription glasses or contact lenses. In most cases, a reading correction is required, such as the use of bifocals. However, many patients find bifocals to be difficult to become accustomed to or uncomfortable.

The EVE procedure and apparatus summarized hereabove and described in applicants' prior U.S. Pat. No. 5,437,678 (Sorensen), U.S. Pat. No. 5,690,641 (Sorensen et al.) and U.S. Pat. No. 5,871,492 (Sorensen) is unique in that it may be useable to treat presbyopia as well as cataracts. This is so because the EVE procedure leaves the main part of the anterior aspect of the lens capsule as well as the ligamentous attachments between the lens capsule and the ciliary muscles, intact. Also, with the EVE procedure no trauma to the endothelium (inner lining of the cornea) is expected because the entire procedure is performed inside the lens capsule. Because the lens capsule remains substantially intact and capable of accommodation, an elastic lens prosthesis can be introduced into the intact lens capsule through the same 1–3 mm opening through which the native lens had been removed by the probe. Thereafter, the normal contractions and relaxations of the ciliary muscles may cause flexing or movement of the lens capsule and resultant changes in the shape of the elastic prosthetic lens, in the same manner as did the crystalline lens before it underwent its age-related stiffening. In this manner, the procedure, in conjunction with a flexible prosthetic lens, may be used as a treatment for presbyopia. This aspect of the procedure, including the introduction of a flexible lens replacement such as a flowable/injectable lens material, are claimed in applicants' U.S. Pat. No. 5,437,678 (Sorensen), U.S. Pat. No. 5,690,641 (Sorensen et al.) and 5,871,492 (Sorensen).

Currently, there remains a need for further improvement and refinement of the devices and procedures used in for surgical removal of the ophthalmic lens so as to further advance the state of the art and the use of such devices to treat disorders of the eye such as cataracts and presbyopia.

SUMMARY OF THE INVENTION

The present invention provides a device for reducing an ophthalmic lens within the lens capsule in a mammalian eye. In accordance with one aspect of the invention, the device includes an elongate probe insertable into the lens capsule. The probe is defined by an outer tubular sheet comprising a hollow bore extending therethrough, and defining a longitudinal axis. An impeller shaft is disposed in the outer tubular sheath and has an impeller on a distal end thereof, wherein an axis of rotation of the impeller is generally coincident with longitudinal axis. The outer tubular sheath is configured and positioned, during operation of the device, such that a distal portion of the sheath will shield a portion of the impeller while allowing a remainder of the impeller to contact and reduce the lens.

In another aspect, the invention provides a device for reducing an ophthalmic lens within the lens capsule in a mammalian eye. The device has an elongate probe insertable into the lens capsule and defining a longitudinal axis. The probe includes an impeller shaft at least partially disposed in a sheath, the impeller shaft having an impeller disposed at a distal end thereof. An axis of rotation of the impeller shaft is generally co-incident with the longitudinal axis of the probe. The device further includes a handpiece having an interior space into which a proximal portion of the elongate probe extends. A drive assembly within the handpiece interior space is functionally connected to a proximal portion of the impeller shaft such that the impeller shaft rotates upon operation of the drive assembly. The drive assembly is adapted to receive non-rotational energy and transmit rotational energy to the impeller shaft.

In a further aspect of the invention, a device for reducing an ophthalmic lens within the lens capsule in a mammalian eye comprises an elongate probe insertable into the lens capsule and defining a longitudinal axis. The probe comprises an impeller shaft having a lens-reducing head disposed at a distal end thereof, wherein an axis of rotation of the impeller shaft is generally co-incident with the longitudinal axis of the probe. A handpiece having an interior space, a front end, and a back end, receives a proximal portion of the elongate probe. Additionally, a pneumatic drive assembly disposed in handpiece interior space includes a turbine, wherein a direct drive connection transfers rotational energy from the turbine to the impeller shaft.

A device for reducing an ophthalmic lens within the lens capsule of mammalian eye accordance with the present invention includes an elongate probe insertable into the lens capsule and defining a longitudinal axis. The probe comprises an impeller shaft having a lens-reducing head disposed at a distal end thereof, wherein an axis of rotation of the impeller shaft is generally co-incident with the longitudinal axis of the probe. A handpiece having an interior space, a front end, and a back end, receives a proximal portion of the elongate probe. A drive assembly is disposed in the handpiece interior space and functionally connects to a proximal portion of the impeller shaft such that the impeller shaft rotates upon operation of the drive assembly. Finally, a translation apparatus at least partially disposed in the handpiece interior space connects to longitudinally displace the drive assembly.

In another aspect, the present invention provides a device for reducing an ophthalmic lens within the lens capsule of mammalian eye including an elongate probe insertable into the lens capsule. The probe comprises an outer tubular sheath having a hollow bore extending therethrough, a hollow impeller shaft having a lumen disposed in the outer tubular sheath and having an impeller disposed at a distal end thereof, an irrigation tube position within and rotationally fixed with respect to the tubular sheath, and a bearing disposed between the impeller shaft and the irrigation tube. The device further includes a handpiece having an interior space into which a proximal portion of the elongate probe extends. A drive assembly is provided for rotating the impeller shaft. An irrigation channel formed within the handpiece interior space is in fluid communication with an annular space formed in the elongate probe between the irrigation tube and impeller shaft. Finally, an aspiration channel formed in the handpiece interior space is in fluid communication with the lumen of the impeller shaft.

In a still further aspect, present invention provides a medical device having an elongate probe insertable into a body and defining a longitudinal axis. The probe has a hollow shaft defining a lumen therein and has a tool disposed at a distal end thereof. An axis of rotation of the tool is generally coincident with the elongate probe axis. A handpiece having an interior space and a front end receives a proximal portion of the elongate probe. A drive assembly disposed in the handpiece interior space is connected to a proximal portion of the impeller shaft such that the shaft rotates upon operation of the drive assembly. An irrigation channel within the handpiece interior space is in fluid communication with an irrigation conduit formed in the elongate probe. An aspiration channel disposed in the handpiece interior space is in fluid communication with the lumen of the impeller shaft. In addition, a fluid block about the impeller shaft between the drive assembly and the handpiece front end provides a barrier between the irrigation channel and the aspiration channel.

In a further aspect of the invention, a variable speed pneumatic turbine system is provided, comprising a turbine in a housing, and a pneumatic system. The pneumatic system includes a pneumatic energy source and a pneumatic delivery line functionally connecting the pneumatic energy source to a orifice in the turbine housing. The orifice is designed to impinge a gas stream from the pneumatic energy source onto the turbine. The turbine system further includes a pneumatic energy controller functionally connected the pneumatic system and capable of controlling delivery of first, second, and third zones of pneumatic energy to the turbine. The first zone comprises pulses of pneumatic energy capable of overcoming stiction of the turbine. The second zone comprises a second zone level of pneumatic energy that is sufficient to sustain rotation of the turbine combined with pulses of pneumatic energy that would overcome stiction if the turbine were to stop rotating. Finally, the third zone comprises a variable level of pneumatic energy that is at least as high as the second zone level of pneumatic energy.

Still further objects and advantages attaching to the device and to its use and operation will be apparent to those skilled in the art from the following particular description.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIGS. 3a and 3b (slightly enlarged) are longitudinal cross-sectional views of the lens-removing device of FIG. 2, with its drive assembly and lens-reducing impeller in their retracted positions.

FIG. 3c is an enlarged partially cut-away perspective view of the distal tip of the lens-removing device showing a lens-reducing head in its retracted position, corresponding to the configuration of the device in FIGS. 3a/3b.

FIGS. 4a and 4b (slightly enlarged) are longitudinal cross-sectional views of the lens-removing device of FIG. 2, with its drive assembly and lens-reducing head in their advanced positions.

FIG. 4c is an enlarged cross-sectional view of the distal tip of the lens-removing device showing the lens-reducing head in its advanced position, and taken within circle 4c–4c of FIG. 4a.

These and additional embodiments of the invention may now be better understood by turning to the following detailed description wherein an illustrated embodiment is described.

DETAILED DESCRIPTION OF THE INVENTION

The following sets forth a description of the invention with reference to a presently preferred embodiment of the invention shown in FIGS. 1–12. The description of the preferred embodiment is intended to serve as an example of the invention, and is not intended to limit the scope of the invention in any way.

Figure 1:
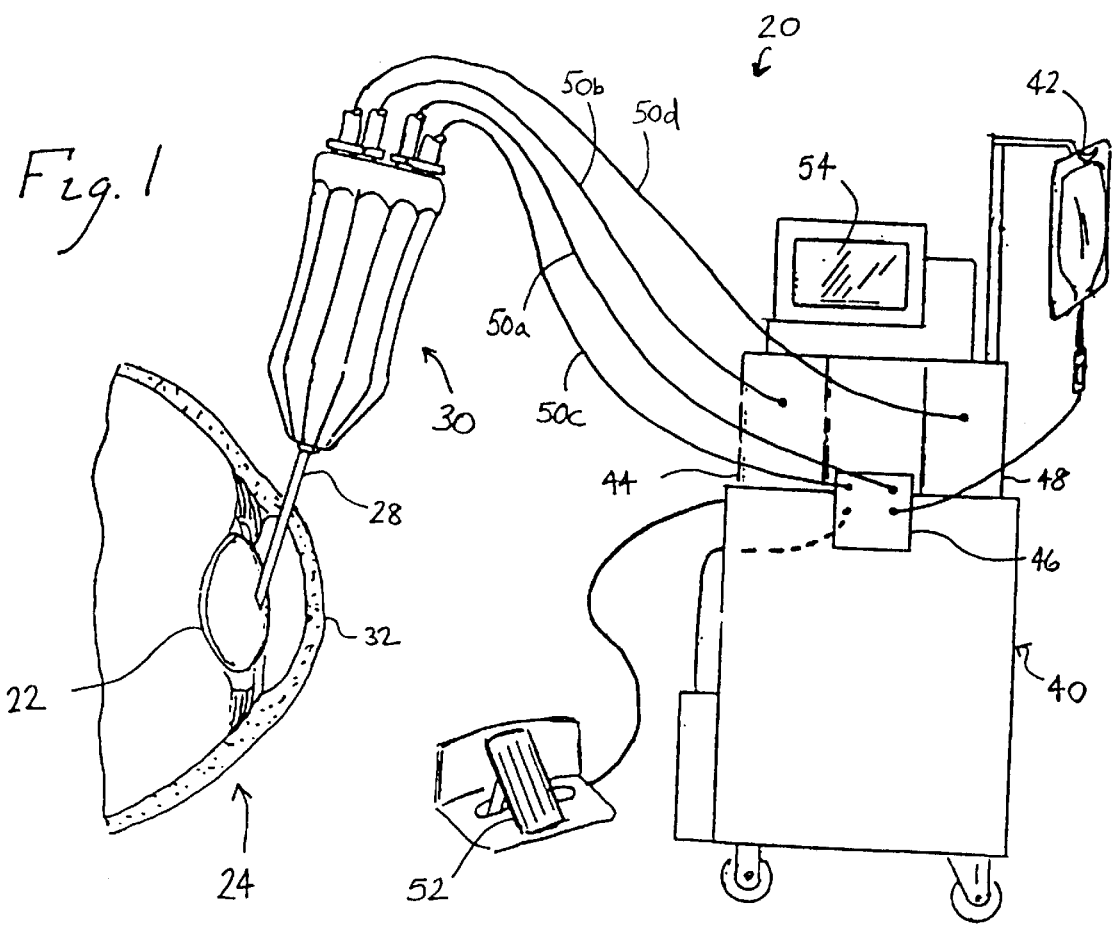
FIG. 1 schematically shows of a lens removal system of the present invention operatively positioned in relation to a human eye.
Figure 1A:
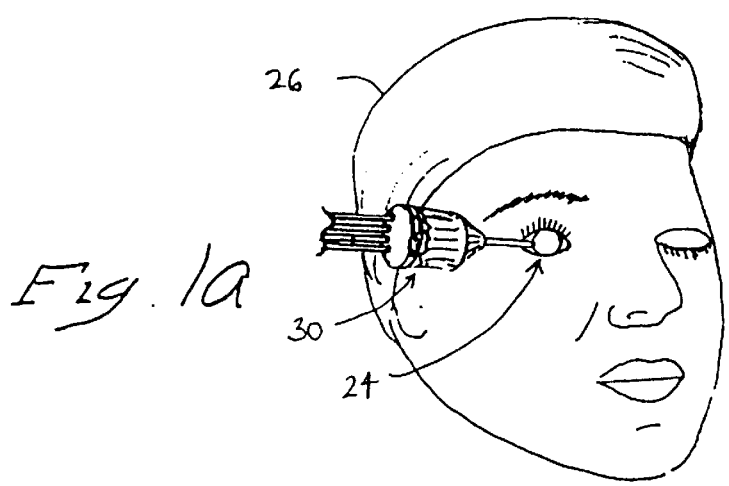
FIG. 1a is a perspective view of the head of a human patient showing a lens reducing probe of a lens-removing device of the present invention inserted for removal of the lens from the patient's left eye.

FIGS. 1 and 1a illustrate a system 20 that can be operated by a surgeon to remove a lens from a lens capsule 22 in an eye 24 of a patient 26. An elongate lens-reducing probe 28 of a lens-removing device 30 is inserted at an angle into the eye 24. More specifically, the elongate probe 28 is inserted at an angle through the cornea 32 and through the lens capsule 22 of the eye 24. A preferred angle is 9:00 as seen from the front into the right eye as shown, or 3:00 into the left eye. An impeller morcellates the lens within the lens capsule and the lens particles are aspirated, as discussed in more detail below.

The lens removing device 30 is connected to a control station 40 that is also part of the system 20. The control station 40 comprises a gravity irrigation feed 42 and control modules 44, 46, and 48. The gravity irrigation feed 42 is an elevated bag filled with a sterile balanced salt solution (BSS) that is delivered to the device 30 through an irrigation fluid tube 50a. Other embodiments of the invention may use a pump to feed the irrigation fluid to the device 30.

The modules 44,46, and 48 of the system control station 40 control the operation of the lens-removing device 30 and the aspiration of the eye 24. The module 44 supplies actuation fluid (i.e., a gas or liquid), preferably a gas such as filtered air, to the device 30 through the tube 50b. The introduction of actuation fluid into the device 30 translates the device from a shielded position to a non-shielded position, as is discussed below. The module 46 controls the aspiration of fluid and particles from the eye 24 through tube 50c. The aspiration module 46 comprises a pump to perform the aspiration. In a preferred embodiment of the invention, the device 30 is powered by a pneumatic turbine located in the device (see FIGS. 4 and 5). A module 48 controls a turbine drive fluid (i.e., a gas or liquid and preferably a gas such as filtered air) being delivered to the device 30. The details of the delivery of the turbine drive fluid are discussed below.

An operator controls the modules 44,46, and 48 via a foot pedal 52 of the system control station 40. If the operator depresses the foot pedal 52 down, the module 48 increases the speed of an impeller in the elongate probe 28 (see FIGS. 3 and 4). Likewise, if the operator releases the foot pedal 52 and permits it to rise, the module 48 decreases the speed of the impeller. The speed of the impeller is displayed on a screen 54 of the control station 40. The device 30 can be made to transition between shielded and non-shielded positions by laterally moving the foot pedal 52. In one embodiment of the invention, the device 30 is placed in the non-shielded position when a predetermined impeller speed is achieved.

Figure 1B:
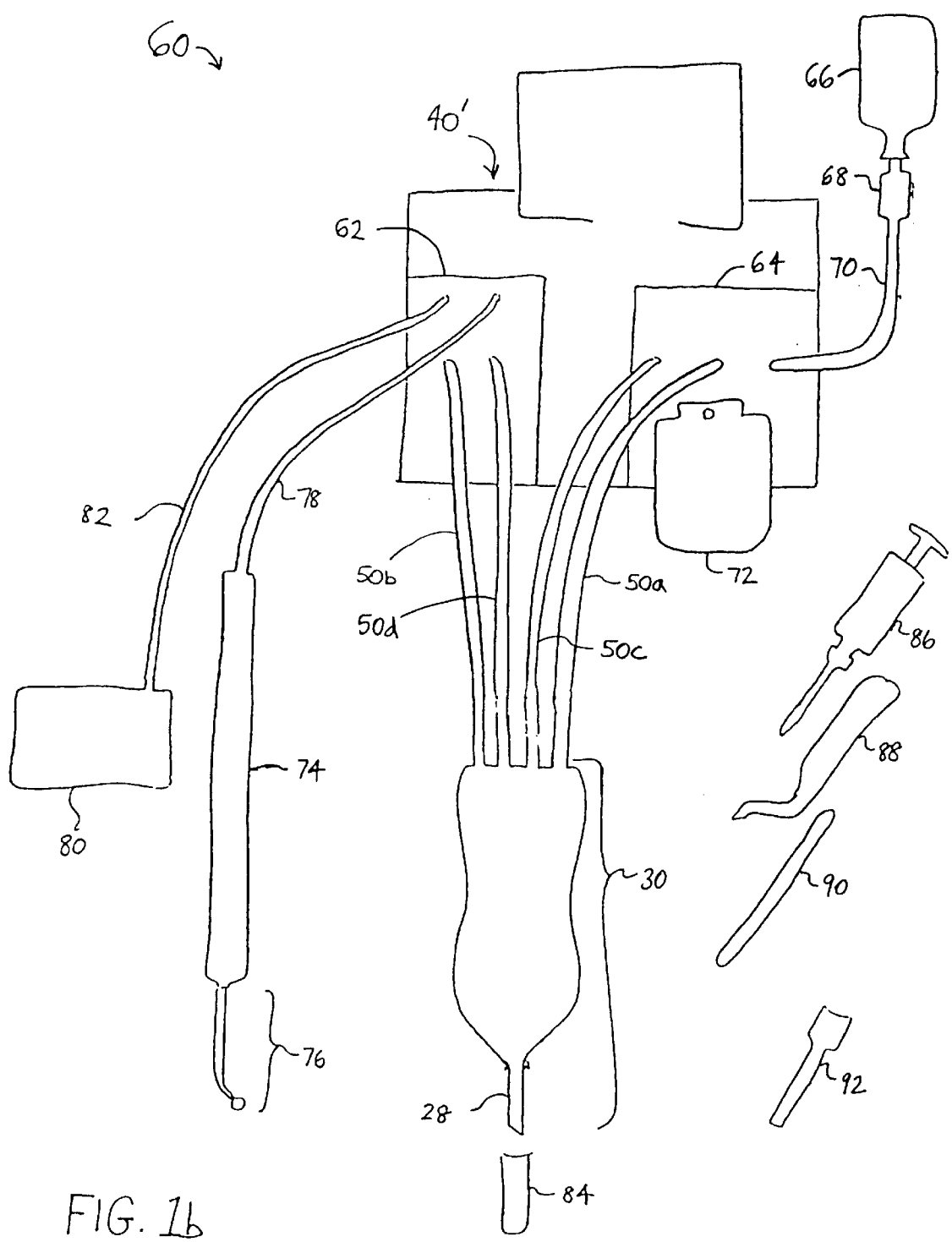
FIG. 1b is a schematic view of a lens removal system of the present invention incorporating the lens-removing device of FIG. 1 and including desirable accessories.

With reference now to FIG. 1b, a lens-removal system 60 including accessories is schematically shown. The system 60 incorporates a control station 40', that is a slightly modified version from the control station 40 shown in FIG. 1. The control station 40' includes an electro-pneumatic module 62 seen on the left side in FIG. 1b, and an aspiration pump module 64 seen on the right side.

The aspiration pump module 64 is a combination of modules 42 and 46 of FIG. 1, and incorporates flow passages and controls for both irrigation and aspiration. More particularly, the aspiration pump module 64 receives a sterile balanced salt solution (BSS) from a bottle 66 suspended thereabove for gravity drainage. The BSS passes through a combination bottle spike/vent/filter device 68 and a tube 70 having a roller shut-off clamp (not shown) before reaching the module 64. The module 64 delivers the BSS to the irrigation tube 50a in communication with a proximal end of the lens-removing device 30. The aforementioned aspiration tube 50c returns aspirated fluid and particles from the device 30 to the aspiration pump module 64. The aspirated matter is then deposited in a collection bag 72.

The electro-pneumatic module 62 includes a compressor and associated controls, an electrosurgical generator, and respective power supplies, module interfaces, and associated hardware. The compressor supplies gas to both an actuation gas tube 50b and a turbine drive gas delivery tube 50d. The tubes 50b and 50d are in communication with the proximal end of the lens-removal device 30, and supply pneumatic power to mechanisms therein which will be described in more detail below. An electrosurgical handpiece 74 having a probe 76 is electrically connected with the module 62 via cable 78. In addition, an electrosurgical antenna plate 80 is electrically connected with the module 62 via cable 82.

The system 60 further includes a number of accessories to facilitate removal of a patient's lens. A purge chamber 84 is shown exploded from the distal end of device probe 28. The purge chamber will be described in more detail below with respect to FIG. 12. Various hand-held instruments are also provided for the system 60, including a viscoelastic 86, a slit knife 88, a capsulotomy sizing probe 90, and a hydrodissection needle 92.

Figure 2:
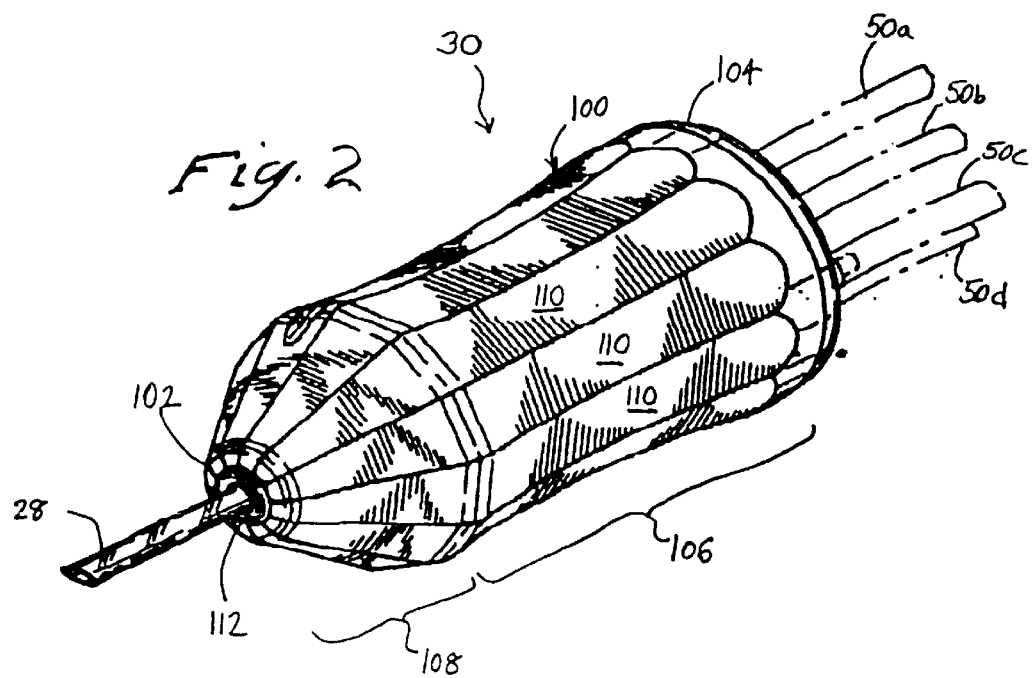
FIG. 2 is an enlarged perspective view of the lens-removing device of the system shown in FIG. 1.

The lens-removing device 30 is seen in FIG. 2 and comprises a handpiece 100 having a distally located front end 102 (to the left) and a proximally located rear cap 104 (to the right). The handpiece 100 has an approximately cylindrical body 106 extending from the rear cap 104 and terminating in a frustoconical portion 108 The front end 102. As is clear from drawings, the exterior of the handpiece 100 includes a plurality of longitudinally extending facets 110 for ease of manipulation by a surgeon.

The elongate probe 28 extends centrally from the front end 102 of the handpiece 100. More specifically, the elongate probe 28 extends through an apex hole 112 at the apex of the frustoconical portion 108. The general appearance of one embodiment of this handpiece 100 is disclosed in co-pending United States design patent application Ser. No. 09/100,749, filed on Feb. 17, 1999 entitled Cataract Removal Device.

The four tubes 50a–50d extended proximally from the rear cap 104 of the handpiece 100. In particular, the irrigation fluid tube 50a for delivering irrigation fluid to the device 30 is seen at the top. Below tube 50a is shown tube 50b that delivers actuation gas to the device 30. Aspirated fluid and debris are removed from the device 30 through aspirated tube 50c. Finally, partly seen below and behind tube 50c is the tube 50d for delivering turbine drive gas to the device 30.

FIGS. 3a/3b and 4a/4b are longitudinal sections through the device 30 shown in, respectively, a retracted, insertion position and an advanced, operative position. In addition, details of the distal end of the elongated probe 28 are shown enlarged in FIGS. 3c and 4c, corresponding to the retracted and advanced positions. For the purpose of this discussion, the proximal orientation is to the right, and the distal orientation is to the left for the components of the device 30.

With reference first to FIGS. 3c and 4c, the elongate probe 28 of the device 30 comprises an outer sheath 120 and an impeller shaft 122 (both preferably tubular) concentrically nested therein. In the illustrated embodiment, the hollow sheath 120 and shaft 122 are generally cylindrical in shape, whereas other embodiments of the invention may have a sheath or a shaft of a different shape. For example, it will be appreciated that in some embodiments of the invention, a solid impeller shaft may be used in place of the hollow impeller shaft 122.

As seen in FIG. 3a, the elongate probe 28 has a fixed distal length 124 that extends distally from the apex hole 112 (FIG. 2) of the handpiece body 106. The impeller shaft 122 has a distal end on which an impeller 128 (lens-reducing head) is integrally formed from the side wall of the hollow impeller shaft (see FIG. 8). Other embodiments of the invention may have an impeller that is not integrally formed on the impeller shaft. The impeller shaft 122 is desirably formed from a relatively rigid biocompatible metal, although alternative embodiments may have an impeller tube or shaft that is not metal, or is flexible to permit a curved elongate probe 28.

As best seen in FIG. 3c, the sheath 120 has a distal portion terminating at a distal end in an angled, generally oval-shaped mouth 130. The mouth 130 includes an apex 132 that defines the distal most extent of the sheath 120. The mouth 130 is desirably planar and forms angle of between 30–60 degrees with a longitudinal axis through the probe 28. Other embodiments of the mouth 130 may be concavely or convexly curved.

FIG. 3c shows that when the device 30 is in the retracted position, the impeller 128 is fully shielded by the sheath 120. That is, the impeller 128 is disposed fully within the sheath 120, proximal with respect to an imaginary surface extending across the mouth 130. FIG. 4c shows the impeller in the advanced position, only partially shielded by the sheath 120. More specifically, at least a portion of the impeller 128 projects beyond the imaginary surface extending across the mouth 130. Desirably, however, the distal most portion of the impeller 128 remains proximal to the apex 132. Of course, FIG. 4c is a sectional view in which the apex 132 is shown behind the impeller 128, and the opposite side of the mouth 130 is not shown at all, so that the projection of the impeller 128 beyond the mouth 130 is not explicitly illustrated. In general, it will be understood that at least a portion of the impeller 128 projects beyond the distal mouth 130 of the sheath 120 in the advanced, operable position of the device 30.

The partial shielding of the impeller 128 during operation directs the flow of fluid entrained by the impeller, as described below. The described configuration and arrangement of the sheath distal portion 130 and the position of the impeller 128 is also disclosed in U.S. Pat. No. 5,871,492 to Sorensen, entitled "Rotary Device for Removing Ophthalmic Lens," which is incorporated herein by reference in its entirety.

The elongate probe 28 provides both irrigation and aspiration during operation of the device 30. In this regard, and as best seen in FIG. 4c, the probe 28 also includes an irrigation tube 134 that extends concentrically within and in close proximity to the outer sheath 120. The irrigation tube 134 is adapted to slide within the sheath 120, and a tubular irrigation channel 136 in the probe 28 is defined between the impeller shaft 122 and the irrigation tube 134. Furthermore, the hollow impeller shaft 122 defines a lumen 138 (see FIG. 3c) therein that is used as an aspiration channel, as will be described below.

Details of the handpiece 100 will now be explained with reference to FIGS. 3a–3c and 4a–4c. The sheath 120 has a proximal portion that extends into the handpiece 100 is fixedly connected to an interior surface 154 of the apex hole 112 using adhesive, or similar expedient. The irrigation tube 134 continues through the apex hole 112 and an O-ring 156 disposed in the interior of the handpiece 100 provides a sliding seal therearound. A proximal end of the irrigation tube 134 extends into a turbine drive assembly 170 disposed in the handpiece 100. More specifically, as best seen in FIGS. 3b and 4b, the irrigation tube 134 proximal end extends through an axial bore in a turbine housing 172 of the turbine drive assembly 170. The turbine housing 172 is held from rotation within the handpiece 100 but can translate axially therewithin.

With specific reference to FIGS. 3b and 4b, a proximal portion of the impeller shaft 122 extends into the turbine drive assembly 170, and rotates about a pin bearing (not numbered) in the center of a backing disk 174. In the illustrated, and preferred, embodiment of the invention, the impeller shaft 122 fits tightly in a central bore of a drive sleeve 176, thus providing a direct drive connection between the shaft and the turbine. As will be explained, the turbine drive assembly 170 receives non-rotational energy and transmits rotational energy to the impeller shaft 122, as disclosed below. The direct drive connection has the advantage of reducing the parts and the size of the turbine drive assembly 170. Other embodiments of the invention may have gear boxes or other devices to transmit the rotational energy to the impeller shaft 122.

As mentioned above, the elongate probe 28 provides irrigation and aspiration during operation of the device 30. Irrigation fluid enters the device 30 through an irrigation port 178, shown at the upper side of the rear handpiece cap 104. Extending distally from the irrigation port 178 is an irrigation channel 180 in communication with the tubular space 136 in the elongate probe 28 between the irrigation tube 134 and the impeller shaft 122 (see FIG. 4c).

Figure 10:
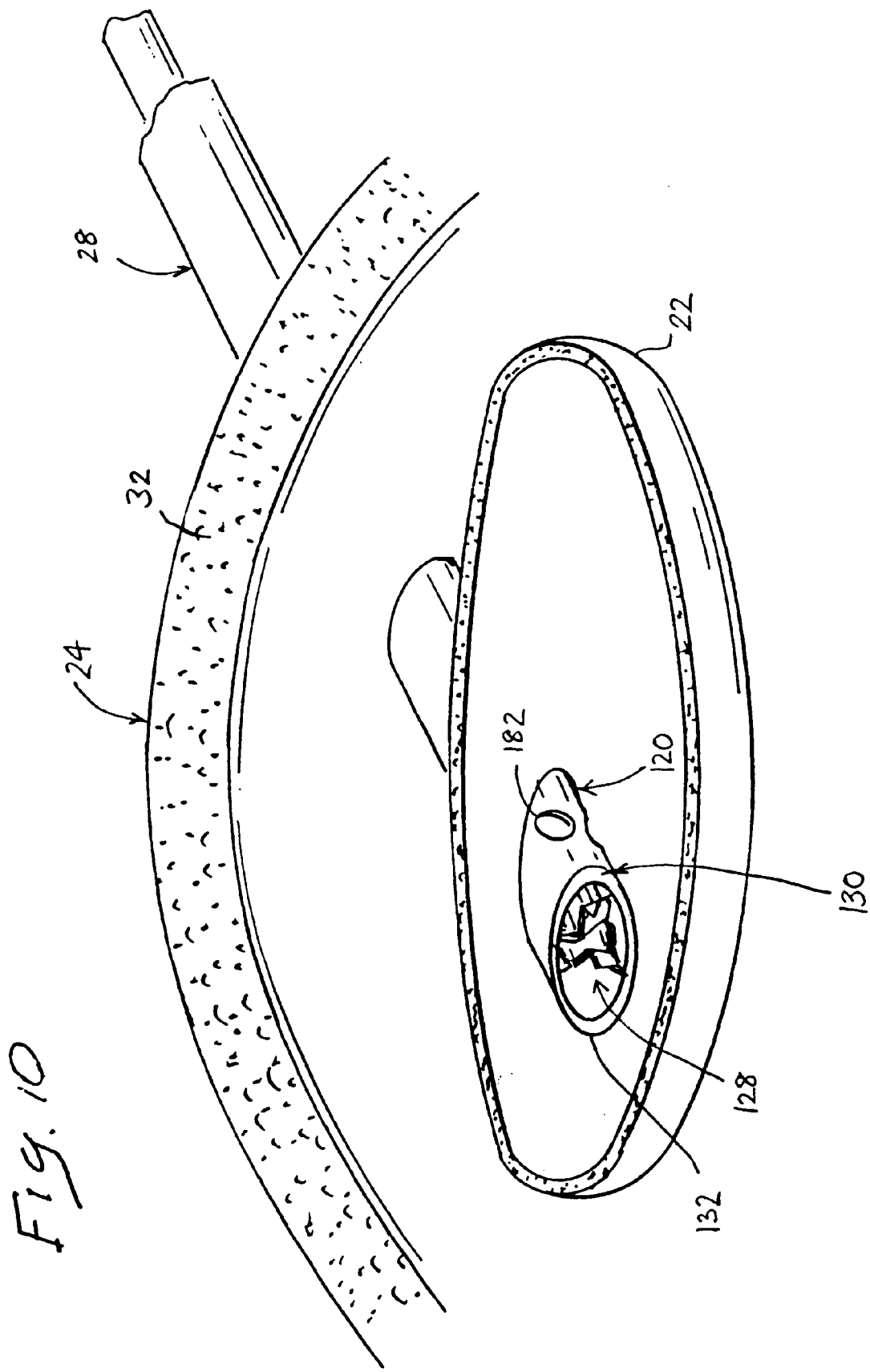
FIG. 10 is a sectional view through the lens capsule and cornea of a mammalian eye, wherein a lens-reducing probe of the present invention has been operatively inserted thereinto to effect endocapsular rotary emulsification of the lens.

In the preferred embodiment of the invention, as illustrated in FIGS. 3c, 4c and 10, irrigation fluid flows distally in the tubular space 136 and out of the elongate probe 28 through holes 182 extending through the sheath 120. The two holes 182 extend through the sheath 120 proximate to the mouth 130, and are longitudinally positioned adjacent each other. At least in the advanced, operable position of the shaft 122, the irrigation fluid does not flow out of the distal mouth 130 of the sheath 120 due to a fluid block bearing 184. The bearing 184 provides a seal between the shaft 122 and the irrigation tube 134, and is positioned axially between the holes 182 and the mouth 130 in the advanced position of the device 30, as in FIG. 4c. The fluid block bearing 184 is generally tubular and supports the shaft 122 in the irrigation tube 134. Other embodiments of the invention may have impeller shaft bearings that permit the irrigation fluid to flow out of the sheath distal end or not have impeller shaft bearings.

In the shown and preferred embodiment of the invention, aspiration fluid is drawn by the impeller 128 into the lumen 138 of the impeller shaft 122. The impeller shaft distal end has a strainer 320 (See FIG. 9) in the lumen 138 that prevents particles from traveling into the handpiece 100 but permits fluid to pass therethrough. Fluid from the procedure is also aspirated into the impeller shaft lumen 138 through holes 324 proximate the impeller shaft distal end. A preferred embodiment of the strainer 320 and holes 324 is discussed in connection with FIG. 9. Other embodiments of the invention may have the impeller shaft distal end plugged (not shown) using any suitable means. In a preferred embodiment of the invention, the plug is a liquid that has hardened.

The aspirated fluid exits the impeller shaft lumen 138 through one or more holes 186 (FIG. 3a) extending through the wall of the tubular shaft 122. The hole 186 is located within the turbine drive assembly 170 and the lumen 138 is sealed proximate to the hole. The hole 186 is in fluidic communication with an outer aspiration channel 188 that extends axially to an aspiration port 190 (shown in FIG. 3a at the lower portion of the rear handpiece cap 104). As a consequence, aspiration fluid traveling through shaft 122 flows through the hole 186 to the aspiration channel 188, and then to port 190.

Figure 5:
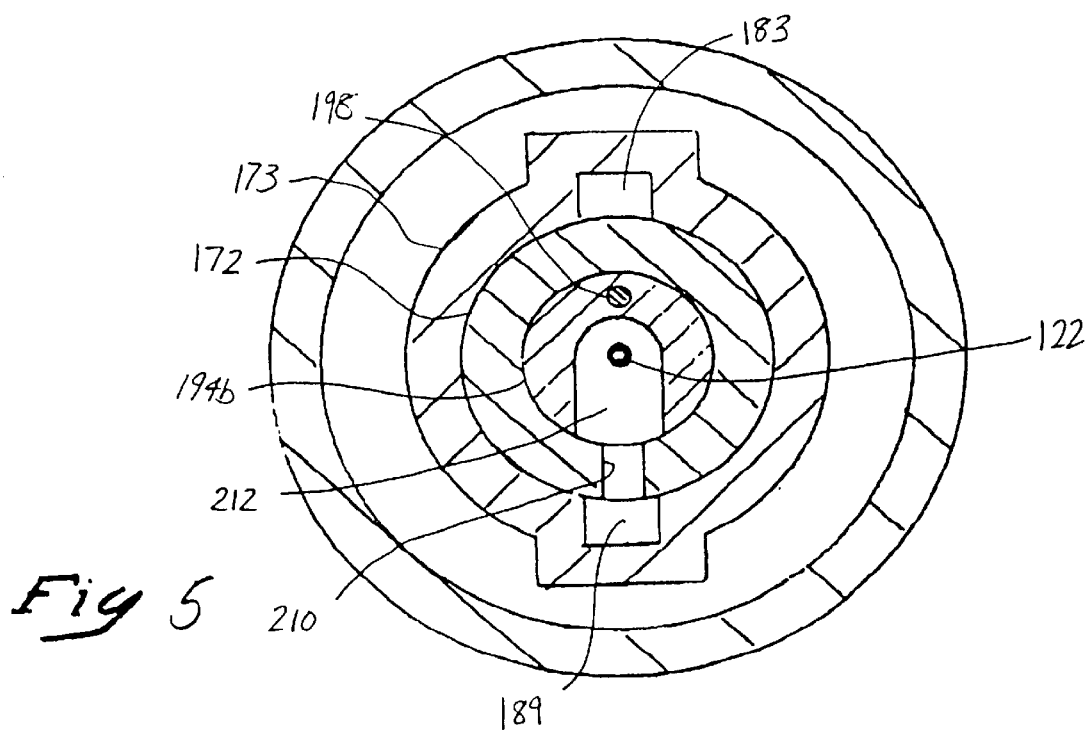
FIG. 5 is a cross-sectional view through line 5—5 of FIG. 3.

Referring now to FIG. 4b in conjunction with FIG. 5, the turbine housing 172 of the turbine drive assembly 170 surrounds a fluid block comprising three identical fluid block bearings 194a, 194b, 194c. The distal bearing 194a is adjacent the distal end of the turbine housing 172 with the bearings 194a–c serially arranged in a proximal direction. Although not shown, each of the bearings 194a–c is clocked in position by a proximally extending post 198 (see FIG. 5) that extends into a complementary hole in a distal face of the adjacent component. The fluid block bearings 194a–c are secured in place with respect to the turbine housing 172 as will be described. The fluid block functions to support the impeller shaft 122 during operation, to seal the operation of the turbine from the operational, distal end of the elongate shaft 122, and to provide a portion of the irrigation and aspiration channels 180 and 188.

Referring to FIGS. 3a, 3b, and 5, the aspiration channel 188 is made up of a number of portions. One portion is a channel 189 formed within a front housing cap 173 that is disposed between the frustoconical portion 108 and the turbine housing 172. Another portion is an aspiration hole 210 that extends through the turbine housing 172 and is in fluidic communication with channel 189. An additional portion of the aspiration channel 188 is a U-shaped gap 212 in the fluid block bearing 194b. The U-shaped gap 212 opens outward into the aspiration port 210 and continues into the fluid block bearing 194b such that the gap is in fluidic communication with an axial hole (not illustrated) in the fluid block bearing and the impeller shaft hole 186. During operation, the aspiration fluid moves from the lumen 138, and outward through the impeller shaft hole 186, the U-shaped gap 212, and the aspiration hole 210, into the channel 189.

The irrigation channel 180 is made up of a number of portions analogous to the aspiration channel 188. Referring now to FIG. 4a, the front housing cap 173 forms a channel 183 that is in fluidic communication with a U-shaped gap 213 in the fluid block bearing 194a. The U-shaped gap 213 is in fluidic communication with the annular space 136 in the elongate probe 28. Irrigation fluid is delivered to the elongate probe 28 through the channel 183 and the U-shaped gap 213.

As seen in FIG. 4a, U-shaped gap 220 in the fluid block bearing 194c forms a first fluid block between the turbine and the operative end of the elongate probe 28. The U-shaped gap 220 is in fluidic communication with the channel 183 of the irrigation channel 180. The fluid block bearing 194c is designed to proximally leak a small percentage of irrigation fluid along the impeller shaft 122 and into a gap formed in the distal turbine bearing 222a. The leaked aspiration fluid exits the gap through a channel (not shown) in the housing 172.

Once irrigation or aspiration fluid enters the U-shaped gaps 212, 213, and 220, beneficial fluidic blocks are formed between the turbine and the operative end of the elongate probe 28. In the shown and preferred embodiment of the invention, the turbine operates pneumatically.

Figure 6:
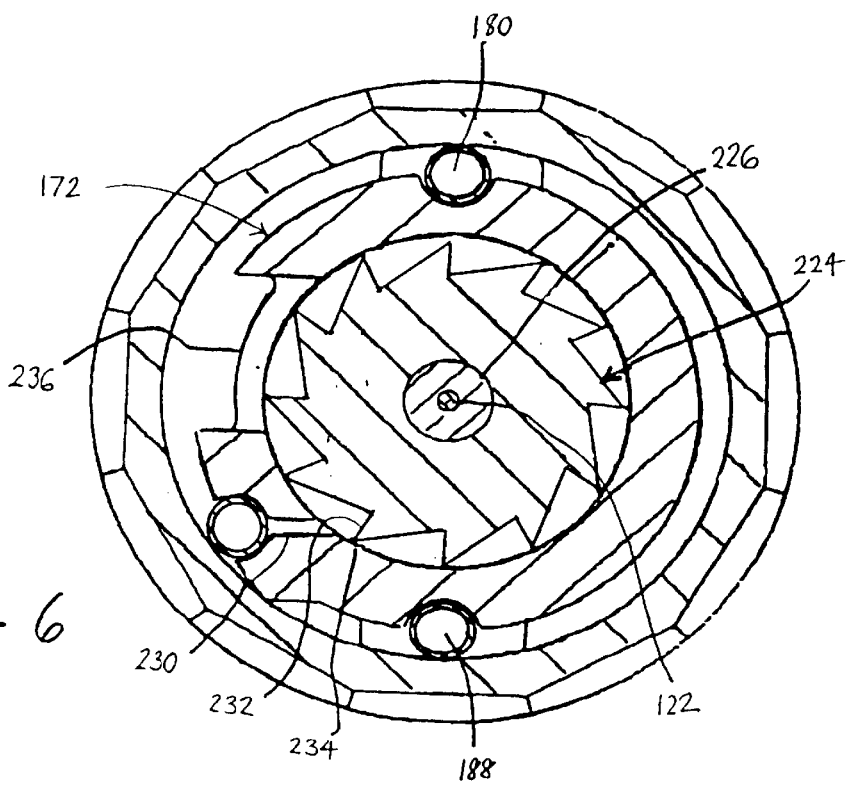
FIG. 6 is a cross-sectional view through line 6—6 of FIG. 3.

Now referring to FIGS. 4b, and 6, the turbine comprises a pneumatically-driven star wheel 224 with the drive sleeve 176 extending therethrough in an interference fit. The star wheel 224 is concentrically disposed in the turbine housing 172 and held in place by opposing, axially positioned turbine bearings 222a, 222b. The impeller shaft 122 extends axially through the drive sleeve 176 and rotates within both bearings 222a,b. A distal flange 228 of the distal bearing 222a contacts the fluid block and axially retains the fluid block bearings 194a, 194b, 194c in place. Other embodiments of the invention may have pneumatic turbines of other designs, or utilize other types of turbines, such as electrical. Still other embodiments of the invention may have drive systems for delivering rotational energy to the device 30, such as is disclosed in U.S. Pat. No. 5,871,492 to Sorensen entitled "Rotary Device for Removing Ophthalmic Lens," which is incorporated herein by reference in its entirety.

Referring specifically to FIG. 6, a compressed gas injector 230 for directing compressed gas onto the star wheel 224 is shown extending through the lower left portion of the turbine housing 172. The injector 230 is arranged to direct a compressed gas stream to perpendicularly strike surfaces 232 of teeth 234 of the star wheel 224. In a preferred embodiment of the invention, a single compressed gas orifice 230 directs a compressed gas stream onto the middle of the surfaces 232. Other embodiments of the invention may have multiple compressed gas orifices either laterally and/or axially spaced apart. A turbine gas exhaust port 236 is shown extending through the turbine housing 172 to the left of the star wheel 224. Preferably, in the embodiment shown, the injector 230 has a progressively decreasing cross-section or lumen diameter, such that the gas or other turbine drive fluid will accelerate as it passes through and out of the injector 230, thereby increasing the velocity with which the gas or other drive fluid impacts the blade surfaces 232.

Figure 11:
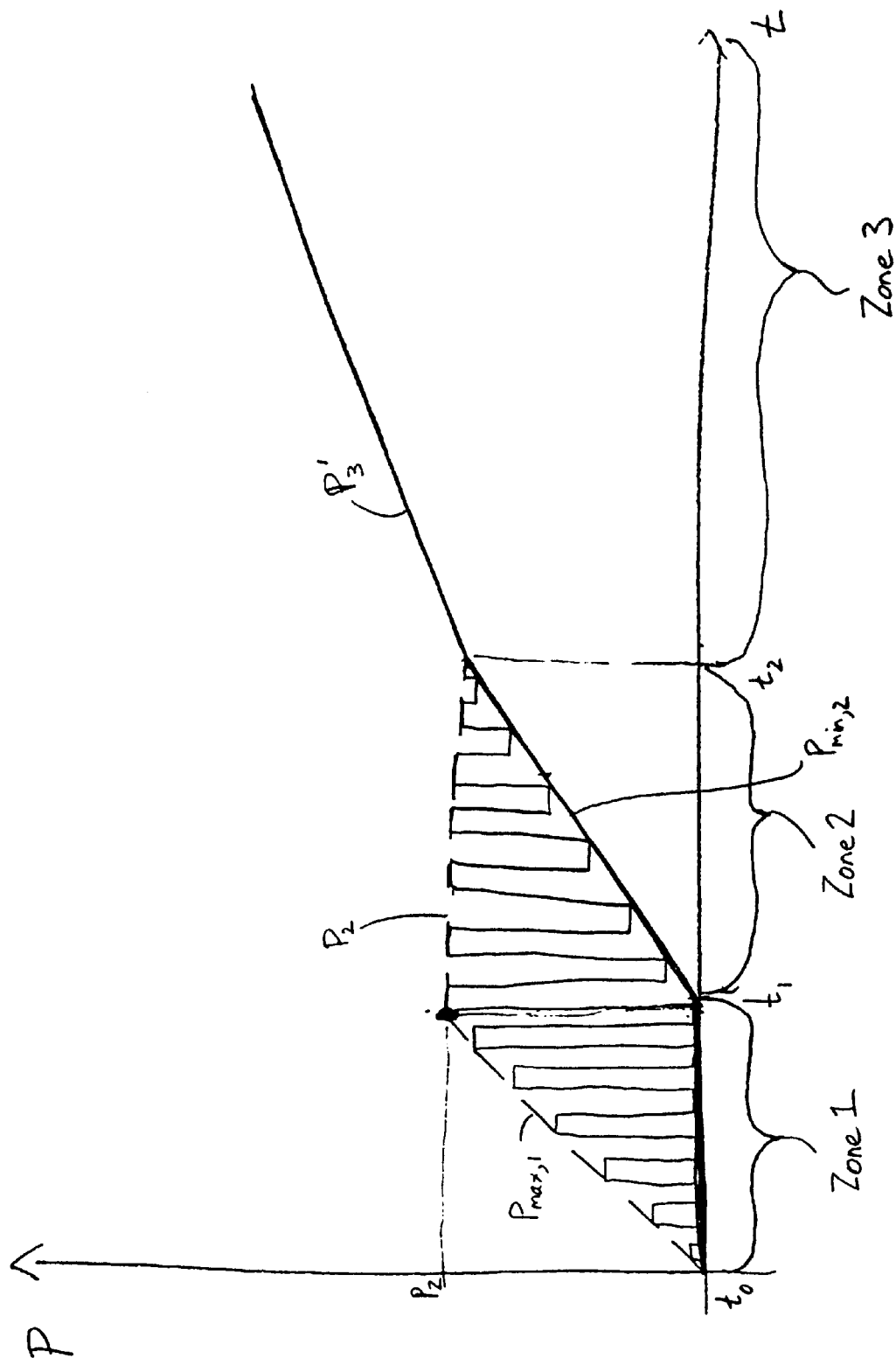
FIG. 11 is a schematic diagram of a pressure waveform for pulsed, anti-stiction acceleration of the turbine to drive the lens reducing head.

FIG. 11 illustrates a preferred pressure waveform exerted on the star wheel 224 to overcome the problem of stiction. Stiction, in this sense, is the common phenomenon affecting rotating machinery whereby the static coefficient of friction exceeds the dynamic coefficient of friction. The preferred waveform shown in FIG. 11 helps initiate rotation of the star wheel 224 from a standstill, but in addition helps prevent premature stalling at low speeds. In small pneumatic motors, such as the turbine illustrated, the rotating element may stall at speeds as high as 10,000 rpm if the pressure wave is constant. The preferred waveform utilizes pulsed air which enables smoother start-ups and rotation at speeds lower than 10,000 rpm.

More specifically, the graph in FIG. 11 shows the pressure applied to the star wheel 224 on the Y-axis, and time along the X-axis. The X-axis is shown divided into three zones; Zone 1 from time $t_0$ to time $t_1$, Zone 2 from time $t_1$ to time $t_2$, and Zone 3 beyond time $t_2$. The pressure wave is seen as a square wave between time $t_0$ and time $t_2$, and then constantly increasing after time $t_2$.

In Zone 1, the pressure wave has a maximum amplitude $P_{max,1}$ that gradually increases from zero to amplitude $P_2$. Also in zone 1, the pressure wave has a minimum or residual amplitude that stays constant at zero. Approaching $t_1$, therefore, the pressure swings increase. After time $t_1$, in zone 2, the pressure wave has a maximum amplitude which stays constant at $P_2$. The minimum or residual amplitude $P_{min,2}$ in zone 2 gradually increases from zero to $P_2$. Approaching $t_2$, therefore, the pressure swings decrease. At time $t_2$ and beyond, in Zone 3, the pressure increases at a constant rate $P_3'$.

The gradually increasing pressure swings in Zone 1 promote even acceleration of the star wheel 224. That is, each burst of pressure is sufficient to impart a small rotational component to star wheel 224 without inducing excessive torsional stresses in the star wheel and connected components which might cause failure. That is, if a pressure $P_2$ was suddenly applied for extended duration to the star wheel 224, the severe change in rotational energy from zero to 35,000 rpm, for example, might be detrimental to the star wheel and/or support bearings. More importantly, a sudden startup of the star wheel 224 may cause failure of the relatively delicate impeller 128. By maintaining the minimum pressure at zero, these excessive startup torques are avoided.

During Zone 2, the minimum pressure $P_{min,2}$ begins to increase while the maximum pressure remains constant at $P_2$. This ramp up gradually increases the average speed of the star wheel 224 to avoid excess torque on the bearings and impeller 128. Ultimately, the inertia of the system reaches a particular magnitude at time $t_2$ so that the input pressure can be increased linearly at rate $P_3'$ during Zone 3.

There are a number of possible waveforms which can be used to pulse the air pressure and produce the even acceleration just described. A preferred waveform is seen in FIG. 11, which is approximately trapezoidal accounting for the slight delay in the pressure delivery system. One example of a waveform is 10 pulses per second. The duration of the pulses can be varied depending on the current rotational speed of star wheel 224. That is, the "duty cycle" of the square waves can be varied depending on the speed of the turbine. The "duty cycle" in this regard pertains to the proportion of time that the star wheel 224 is pressurized. At low levels, the duty cycle might be 80%, while at high levels of rotation the duty cycle might be 20%, reflecting the reduced torque needed to impart a change in speed.

Referring back to FIGS. 3b and 4b, a bladder 240 is used to longitudinally translate the turbine drive assembly 170 between non-shielded and shielded positions. The bladder 240 is disposed between a 242 at the turbine housing back end and the rear handpiece cap 104. The bladder 240 comprises a proximally opening cup-shaped structure having a closed distal end that contacts and acts upon the cap 242. The bladder open end has a inwardly extending radial lip 250 that is sealed in a complementary groove 252 of the rear handpiece cap 104.

Figure 7:
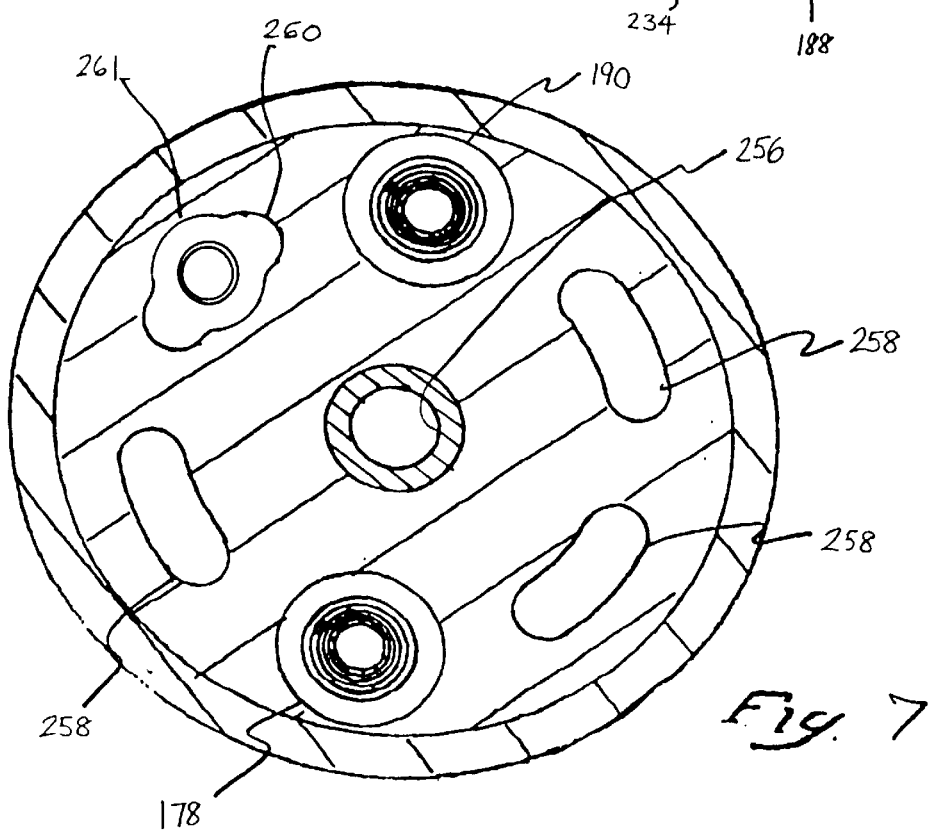
FIG. 7 is a cross-sectional view through line 7—7 of FIG. 3.

Referring to FIGS. 3b and 7, the irrigation port 178 and the aspiration port 190 are located at the top and the bottom of the device rear cap 104 (FIG. 3), respectively. In the center of the rear cap 104 is an actuator gas port 256. Three vents 258 are located in three quadrants of the rear cap 104 and are of a curved, oblong shape. The vents 258 extend through the rear cap 104 and enable spent turbine gas and liquid from the aforementioned gap in the distal turbine bearing 222a to exit the handpiece 100. In the remaining quadrant is a vent 260 of the same general shape as the vents 258 except for a circular region 261. The circular region permits access of the turbine drive gas tube 24d (not shown) to the turbine star wheel 224.

The actuator gas port 256 axially and centrally extends through the rear handpiece cap 104, and is in fluidic communication with an interior 262 of the cup-shaped bladder 240 (see FIG. 4b) facing the rear handpiece cap 104. The actuator gas port 256 is adapted to be connected to the actuator gas tube 24b (see FIG. 1). The tube 24b provides compressed gas to expand the bladder 240 and, thereby, longitudinally translating the turbine drive assembly 170 and the attached impeller shaft 122.

With reference to FIG. 3b, the bladder 240 is shown un-inflated and the device 30 is in the retracted, shielded position. The turbine drive assembly 170 is proximally located in the handpiece 100. The impeller 128 is substantially shielded by the sheath 120, as seen in FIG. 3c.

Linear actuation of the turbine assembly 170 within the handpiece 100 will be described with reference to FIGS. 3b and 4b. Initially, it will be noted that the handpiece rear cap 104 is fixed at the proximal end of the body 106. The irrigation port 178 and aspiration port 190 are each located at the proximal end of an irrigation tube 270 and an aspiration tube 272, respectively. The tubes 270, 272 extend proximally to the turbine housing cap 173, and are fixed to translate with the turbine assembly 170. In this regard, the tubes 270, 272 slide through apertures formed in the rear cap 104.

An irrigation fitting 274 and an aspiration fitting 276 are provided on the proximal ends of the creation tube 270 and aspiration tube 272, respectively, to provide couplings for flexible tubes attached to the handpiece 100. Each of the fittings 274, 276 is sized to fit within counterbores 270, 280 provided in the rear cap 104. The fittings 274, 276 are biased out of the counterbores 270, 280 by coil springs 282, 284 surrounding the tubes 270, 272, respectively. Because of the rigid connection between the fittings 274, 276 and tubes 270, 272, and between the tubes and the rest of the turbine assembly 170, the turbine assembly is biased in a proximal direction by the springs 282, 284. This biased position is indicated in FIG. 3b by a gap 286 between the fitting 276 and a step formed in the recess 280 of the cap 104. Again, the position shown in FIG. 3b is the retracted, non-operable position of the device 30.

FIG. 4b illustrates the device 30 in its advanced, operable position, wherein the 286' and has been significantly reduced. The proximal bias of the springs 282, 284 has been overcome by introduction of gas through port 256 to the interior 262 of the cup-shaped bladder 240. Consequently, the bladder 240 has expanded, pushing in a distal direction on the turbine housing cap 242 and displacing the turbine assembly 170 to its operable position. Various physical limit stops can be provided to halt displacement of the turbine assembly 170, or the bladder 240 can be designed to be fully expanded prior to physical contact between such stops. Again, the advanced position of the device 30 urges the impeller 128 to its partially shielded position, as seen in FIG. 4c.

Figure 8:
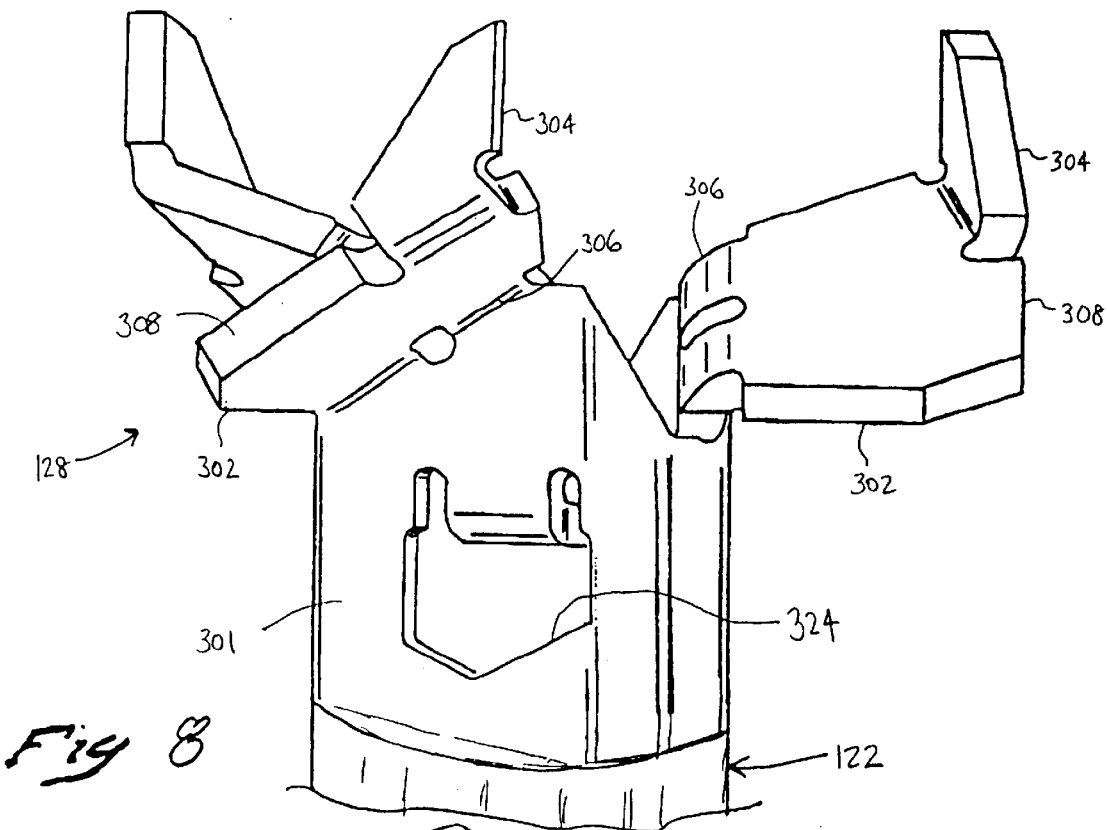
FIG. 8 is a side elevational view of the lens-reducing head of the device of FIG. 3.
Figure 9:
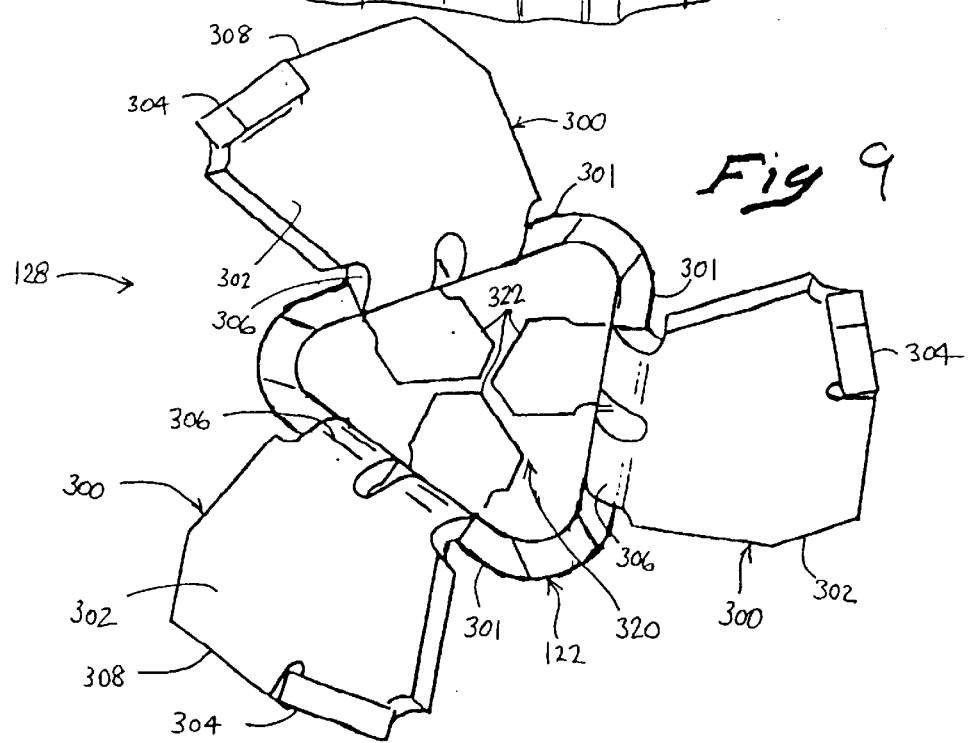
FIG. 9 is a distal end view of the lens reducing head of FIG. 8.

Referring now to FIGS. 8 and 9, the impeller or lens-reducing head 128 in the preferred embodiment of the invention is comprised of three blades 300 integrally formed from the hollow impeller shaft 122. The blades 300 extend from flat portions 301 of the impeller shaft 122, making the impeller shaft distal end approximately triangular in shape with the remainder of the impeller shaft being tubular. Other embodiments of the invention may have impeller tubes or shafts of any shape. Still other embodiments of the invention may have an impeller of more or less blades or an impeller that is attached to the impeller tube or shaft distal end instead of integrally formed therefrom.

The impeller blades 300 are arranged about the impeller shaft distal end, and are identical in size and shape. In the presently preferred embodiment shown, each blade 300 comprises a first portion 302 and a second portion 304. The blade first portion 302 extends approximately radially from the impeller shaft distal end and is pitched. The first blade portion 302 is connected to the impeller shaft 122 via two connector portions 306. The blade second portion 304 extends axially and distally from an outward edge 308 of the blade first portion 302. The blade second portion 304 has a leading edge 310 that is generally parallel to a longitudinal axis 312 of the impeller shaft 122. The impeller 128 is configured to draw a flow of fluid toward the impeller during rotation. Other embodiments of the invention may have blades of other configurations and/or size or impellers that are not configured to draw a flow of fluid. For example, in some embodiments, the second blade portion 304 may be eliminated or modified in shape, on one or more of the blades 300. Also, in some embodiments, the number of blades 300 my vary and/or the tangential spacing, symmetry and/or lack of symmetry of the blades 300 my be varied. Also, in some embodiments, the blades may not all be of the same shape and/or size, but rather may vary in shape and/or size.

The preferred embodiment of the strainer 320 is also shown in FIGS. 8 and 9. The strainer 320 is proximate to the impeller shaft distal end. The strainer 320 is comprised of three symmetrically positioned tabs 322 that extend inward from the three generally flat portions 301 of the impeller shaft 122 and create the aforementioned shaft holes 324. The tabs 322 are integrally formed from the shaft 122 and are bent radially inwardly so as to be disposed in a radial plane. The tabs 322 are sized and shaped to restrict particles from being aspirated through the impeller shaft 122. In the preferred embodiment, the tabs 322 and shaft holes 324 are polygonal, and the tabs have angled points that fit closely together in the shaft lumen 138, as seen in FIG. 9, to help improve the straining effect. A strainer in other embodiments of the invention may have more or less tabs, be of a different configuration, or may not be integral with the impeller shaft 122.

The tabs 322 of the strainer 320 are also sized and shaped to support a drop of liquid through the liquid's surface tension such that the liquid may solidify and form a plug (not shown) in embodiments where it is desired to plug the lumen of the impeller shaft 122 distal to the tabs 322, thereby causing fluid to flow into/out of the shaft 122 only through the side holes created in the shaft by the infolding of the tabs 322. Any suitable liquid that hardens to a plug and resists extraction or mechanical breakdown may be used for this purpose, such as epoxy, resin, or caulk.

The side holes created by the infolding of the tabs 322 will not likely become blocked or clogged because such side holes are located in a shear field as the impeller shaft 122 rotates.

Referring now to FIG. 10, an elongate EVE probe 28 is shown in a position to remove a lens (not shown) from an eye 24. The elongate probe 28 is inserted at an angle through the cornea 32 of the eye 24 and into the lens capsule 34. The impeller 128 is in a non-shielded position and projects beyond the surface defined by the angled mouth 130. Again, however, the impeller 128 remains proximally disposed with respect to the apex 132 of the sheath 120. This partial shielding of the impeller 128 permits the operator of the device 30 to direct the flow of liquid and particles in the lens capsule 22. The flow created by the impeller 128 also helps keep the lens capsule 22 expanded during operation. Additionally, the lens is drawn to the impeller 128 because the impeller draws the flow towards it, resulting in reduced movement of the elongated probe 28 to reach and morcellate the lens. These advantages of the preferred embodiment of the invention reduce the chance that the lens capsule 22 will come into contact with the impeller 128 or the distal end of the sheath 120 and become damaged.

Typically, some gravity feed or positive pressure will be applied to irrigation fluid being infused through the EVE probe 28. However, in the event that the feed or flow of irrigation fluid is momentarily interrupted, the dynamic force of the fluid circulating within the lens capsule 22 will maintain the lens capsule in a fully expanded or non-collapsed state, thereby minimizing the likelihood of iatrogenic laceration or puncture of the lens capsule wall by the rotating lens reducing impeller 128. Additionally, in some embodiments, a flow meter, bubble detector or pressure sensor may be positioned so as to monitor the flow of irrigation fluid and/or the return of aspiration fluid/particles and may be connected to the controller and adapted to automatically stop the rotation of the impeller in the event of any disruption in the flow of irrigation fluid and/or the return of aspiration fluid/particles.

Figure 12:
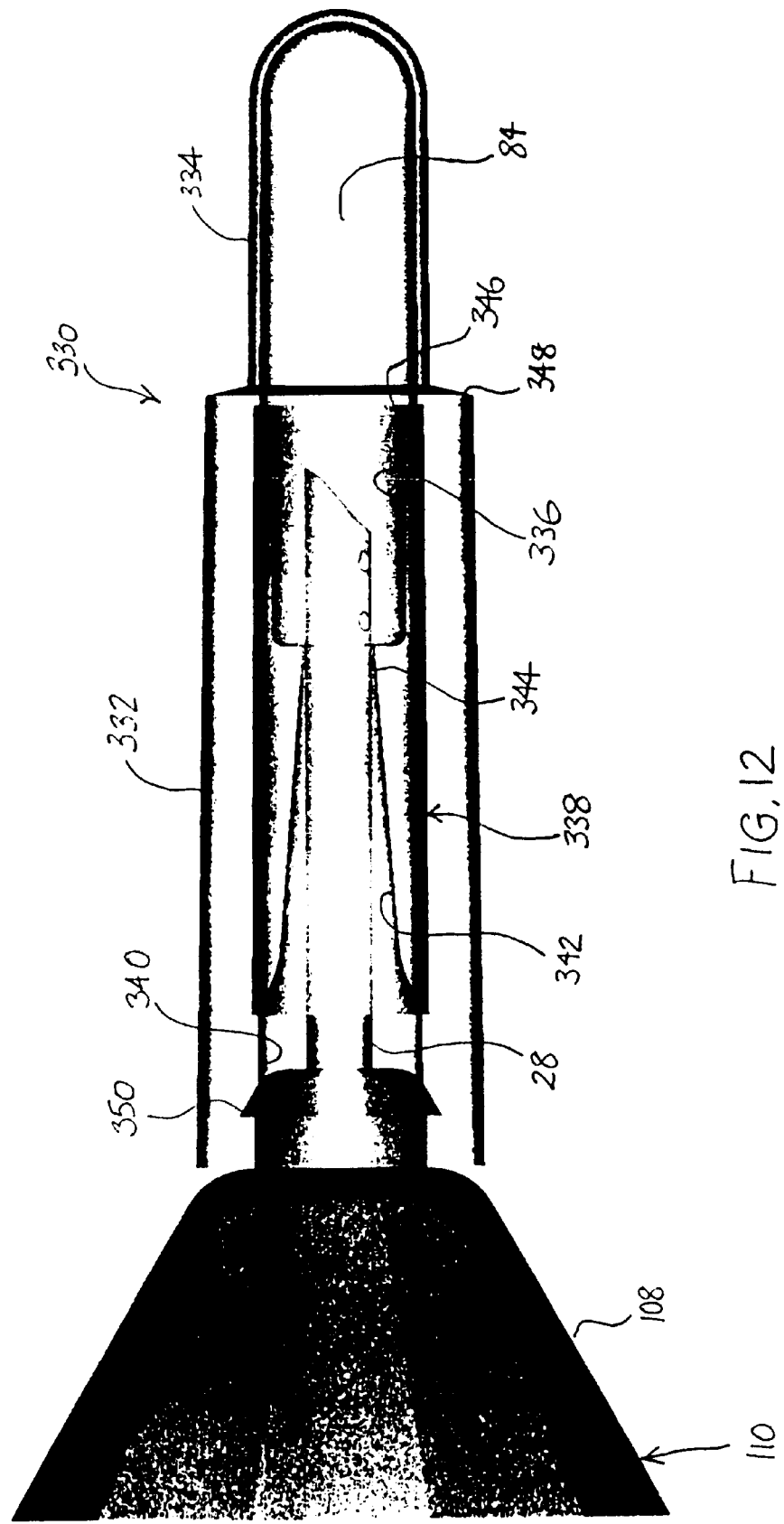
FIG. 12 is an elevational view of a purging chamber and protection cap for use with the lens-removal device of the present invention.

In the embodiment shown, the EVE Probe 28 may include an optional apparatus for protecting the fragile probe 28 and impeller 122 therein, and for facilitating the purging of air from the infusion system just prior to use. In this regard, FIG. 12 shows an optional purge cap 330 that closely receives the probe 28. The purge cap 330 comprises a tubular body 332, an integrally formed collapsible nipple 334, and a rigid insert 336. The aforementioned purge chamber 84 is defined partly within the collapsible nipple 334, and partly within a relief chamber 338 of the rigid insert 336. The rigid insert 336 is tightly received within a through bore 340 of the tubular body 332 and further includes a tapered bore 342 extending proximally from the relief chamber 338. The tapered bore 342 narrows in diameter until it is approximately the same diameter as the probe 28 at a seal portion 344.

The purge cap 330, comprising the tubular body 332 and collapsible nipple 334, is desirably formed of an elastomeric material, such as silicone. The rigid insert 336, on the other hand, is desirably formed of a rigid material, such as polycarbonate or other high-density polymer. The assembly of the purge cap 330 and rigid insert 336 is formed by press fitting the insert into the bore 340 until the distalmost end 346 of the insert is approximately aligned with the distalmost end 348 of the tubular body 332. The assembly is then secured around a probe 28 by an interference fit between the bore 340 and an annular, triangular rib 350 formed at the end of the frustoconical portion 108 of the handpiece 100. The probe 28 is guided through the tapered bore 342 until the distal end resides in a relief chamber 338. A fluid-tight fit between the rigid insert 336 and probe 28 is created at the narrow seal portion 344.

In use, irrigation fluid is circulated through the handpiece 100 and probe 28 to exit into the purge chamber 84. At the same time, the aspiration system is operated to remove the irrigation fluid from within the purge chamber 84. At a predetermined time, the irrigation fluid flow is halted and a high vacuum is drawn within the purge chamber 84. The nipple 334 collapses to indicate to the operator that the vacuum is in effect. The high vacuum tends to expand any bubbles remaining in the device 30, which loosens them and encourages them to migrate through the aspiration channels. This procedure may be repeated more than once for precautionary reasons. Ultimately, the purge cap 330 with the rigid insert 336 is removed from the probe 28 just prior to use of the lens-removal device 30.

It is to be appreciated that the invention has been described hereabove with reference to certain presently preferred embodiments or examples only, and no attempt has been made to exhaustively describe all possible embodiments and examples in which the invention may be practiced. It is to be appreciated that various additions, deletions and modifications may be made to the above-described embodiments or examples without departing from the intended spirit and scope of the invention, and it is intended that all such additions, deletions and modifications be included within the scope of the following claims.

What is claimed is:

1. A device for reducing an ophthalmic lens within the lens capsule of a mammalian eye, said device comprising:
   an elongate probe insertable into the lens capsule, said probe comprising:
   i. an outer tubular sheath comprising a hollow bore extending therethrough and defining a longitudinal axis;
   ii. an impeller shaft disposed in said outer tubular sheath, said impeller shaft having an impeller disposed at a distal end thereof, wherein an axis of rotation of said impeller is generally coincident with said longitudinal axis; and
   iii. said outer tubular sheath being configured and positioned, during operation of said device, such that a distal portion of said sheath will shield a portion of said impeller while allowing a remainder of said impeller to contact and reduce the lens;
   a handpiece having an interior space, a front end, and a back end, wherein an interior portion of said elongate probe extends through said handpiece front end and into said handpiece interior space;
   a drive assembly disposed in the interior space of said handpiece;
   said drive assembly being functionally connected to a proximal portion of said impeller shaft such that said impeller shaft rotates upon operation of said drive assembly, wherein said drive assembly receives non-rotational energy and transmits rotational energy;
   a translation apparatus for longitudinally moving said drive assembly, said translation apparatus being at least partially disposed in said handpiece interior space; and
   wherein said translation apparatus comprises an inflatable bladder disposed between said handpiece back end and said drive assembly.

2. The device of claim 1 herein said device includes structure to cause the drive assembly to retract to a position proximate the back end of said handpiece when said bladder is not inflated.

3. The device of claim 2 wherein said structure comprises at least one spring to bias the drive assembly to the retracted position.

4. A device for reducing an ophthalmic lens within the lens capsule of a mammalian eye, said device comprising:
   an elongate probe insertable into the lens capsule, said probe comprising:
   i. an outer tubular sheath comprising a hollow bore extending therethrough and defining a longitudinal axis;
   ii. an impeller shaft disposed in said outer tubular sheath, said impeller shaft having an impeller disposed at a distal end thereof, wherein an axis of rotation of said impeller is generally coincident with said longitudinal axis; and
   iii. said outer tubular sheath being configured and positioned, during operation of said device, such that a distal portion of said sheath will shield a portion of said impeller while allowing a remainder of said impeller to contact and reduce the lens;
   an irrigation channel comprising an outlet in fluidic communication with a proximal opening in said sheath;
   an aspiration channel comprising an inlet in fluidic communication with a proximal opening in said impeller shaft; and
   an irrigation tube within and rotationally fixed with respect to said tubular sheath, and a bearing disposed between said impeller shaft and said irrigation tube.

5. The device of claim 4 wherein:
   said bearing substantially seals an annular space defined by said irrigation tube and said impeller shaft; and
   a sheath aperture extending through a wall of said sheath and located near said bearing.

6. The device of claim 5 further comprising an impeller shaft aperture extending through an impeller shaft wall and being located proximate to said sheath aperture.

7. The device of claim 6 wherein said impeller shaft is adapted to advance within said sheath from a retracted position, to the operative position wherein a distal portion of said sheath will shield a portion of said impeller, and wherein said impeller shaft aperture is generally aligned with said sheath aperture when said impeller is in the retracted position.

8. A device for reducing an ophthalmic lens within the lens capsule of a mammalian eye, said device comprising:
   an elongate probe insertable into the lens capsule, said probe comprising:
   i. an outer tubular sheath comprising a hollow bore extending therethrough and defining a longitudinal axis;
   ii. an impeller shaft disposed in said outer tubular sheath, said impeller shaft having an impeller disposed at a distal end thereof, wherein an axis of rotation of said impeller is generally coincident with said longitudinal axis; and
   iii. said outer tubular sheath being configured and positioned, during operation of said device, such that a distal portion of said sheath will shield a portion of said impeller while allowing a remainder of said impeller to contact and reduce the lens; and
   a strainer disposed in said impeller shaft proximate to said impeller shaft distal end.

9. The device of claim 8 wherein:
   said impeller shaft comprises a wall; and
   said strainer is comprised of a plurality of tabs that radially extend inwardly from said impeller shaft wall to form said strainer.

10. The device of claim 9 wherein the plurality of tabs comprise three symmetrically positioned tabs that extend generally in a radial plane from three generally flat portions of said impeller shaft.

11. A device for reducing an ophthalmic lens within the lens capsule of a mammalian eye, said device comprising:
    an elongate probe insertable into the lens capsule and defining a longitudinal axis, said probe comprising an impeller shaft at least partially disposed in a sheath, said impeller shaft having an impeller disposed at a distal end thereof, wherein an axis of rotation of said impeller shaft is generally coincident with said longitudinal axis;

a handpiece having an interior space into which a proximal portion of said elongate probe extends;

a drive assembly disposed in said handpiece interior space, said drive assembly being functionally connected to a proximal portion of said impeller shaft such that said impeller shaft rotates upon operation of said drive assembly, wherein said drive assembly received non-rotational energy and transmits rotational energy;

wherein a direct drive connection transfers rotational energy from said drive assembly to said impeller shaft; and wherein said translation apparatus comprises an inflatable bladder disposed between said handpiece back end and said drive assembly.

12. The device of claim 11 wherein said device includes structure to cause the drive assembly to retract to a position proximate the back end of said handpiece when said bladder is not inflated.

13. The device of claim 12 wherein said structure comprises at least one spring to bias the drive assembly to the retracted position.

14. A device for reducing an ophthalmic lens within the lens capsule of a mammalian eye, said device comprising:

an elongate probe insertable into the lens capsule and defining a longitudinal axis, said probe comprising an impeller shaft having a lens-reducing head disposed at a distal end thereof, wherein an axis of rotation of said impeller shaft is generally coincident with said longitudinal axis;

a handpiece having an interior space, a front end, and a back end, wherein a proximal portion of said elongate probe extends through said handpiece front end;

a pneumatic drive assembly disposed in said handpiece interior space, said pneumatic drive assembly comprising a turbine, wherein a direct drive connection transfers rotational energy from said turbine to said impeller shaft;

wherein the turbine comprises a star wheel coupled to rotate with the impeller shaft, and the pneumatic drive assembly includes an injector opening onto the star wheel to direct a flow of gas thereto; and wherein the injector has a progressively decreasing cross-section in a direction toward the star wheel such that gas passing therethrough will accelerate toward the star wheel.

15. The device of claim 14 wherein the impeller shaft is hollow and adapted to aspirate fluid from the lens capsule, the device further including a fluid block surrounding the impeller shaft and preventing mixing of the aspiration fluid and the gas used to turn the star wheel.

16. The device of claim 15 wherein the fluid block comprises a plurality of fluid bearing blocks.

17. A device for reducing an ophthalmic lens within the lens capsule of a mammalian eye, said device comprising:

an elongate probe insertable into the lens capsule and defining a longitudinal axis, said probe comprising an impeller shaft having a lens-reducing head disposed at a distal end thereof, wherein an axis of rotation of said impeller shaft is generally coincident with said longitudinal axis;

a handpiece having an interior space, a front end, and a back end, wherein a proximal portion of said elongate probe extends through said handpiece front end;

a pneumatic drive assembly disposed in said handpiece interior space, said pneumatic drive assembly comprising a turbine, wherein a direct drive connection transfers rotational energy from said turbine to said impeller shaft; and further comprising a translation apparatus for longitudinally moving said drive assembly, said translation apparatus being at least partially disposed in said handpiece interior space wherein said translation apparatus comprises an inflatable bladder disposed between said handpiece back end and said drive assembly.

18. The device of claim 17 wherein said device includes at least one spring to bias the drive assembly to retract to a position proximate the back end of said handpiece when said bladder is not inflated.

19. A device for reducing an ophthalmic lens within the lens capsule of a mammalian eye, said device comprising:

an elongate probe insertable into the lens capsule and defining a longitudinal axis, said probe comprising an impeller shaft having a lens-reducing head disposed at a distal end thereof, wherein an axis of rotation of said impeller shaft is generally coincident with said longitudinal axis;

a handpiece having an interior space, a front end, and a back end, wherein a proximal portion of said elongate probe extends through said handpiece front end;

a drive assembly disposed in said handpiece interior space functionally connected to a proximal portion of said impeller shaft such that said impeller shaft rotates upon operation of said drive assembly;

a translation apparatus at least partially disposed in said handpiece interior space and connected to longitudinally displace said drive assembly; and wherein said translation apparatus comprises an inflatable bladder disposed between such handpiece back end and said drive assembly.

20. The device of claim 19 wherein said device includes structure to cause the drive assembly to retract to a position proximate the back end of said handpiece when said bladder is not inflated.

21. The device of claim 20 wherein said structure comprises at least one spring to bias the drive assembly to the retracted position.

22. The device of claim 19 wherein said wherein said bladder comprises:

a cylindrical wall;

a sealed distal end of said bladder cylindrical wall that is adjacent to a proximal end of said drive assembly, wherein said cylindrical wall and said sealed distal end define a bladder interior; and an open proximal end of said bladder, with a radial inwardly extending lip that is sealed against said handpiece back end.

23. The device of claim 22 further including a port extending through said handpiece back end and adapted for connecting a compressed gas source to said bladder interior to inflate said bladder.

24. The device of claim 19 wherein the impeller shaft is hollow and adapted to aspirate fluid from the lends capsule, the device further including a fluid block surrounding the impeller shaft and preventing mixing of the aspiration fluid and the gas used to inflate said bladder.

25. A device for reducing an ophthalmic lens within the lens capsule of a mammalian eye, said device comprising
- an elongate probe insertable into the lens capsule, said probe comprising:
  - i. an outer tubular sheath having a hollow bore extending therethrough;
  - ii. a hollow impeller shaft having a lumen and disposed in said outer tubular sheath, said impeller shaft having an impeller disposed at a distal end thereof;
  - iii. an irrigation tube positioned within and rotationally fixed with respect to the tubular sheath; and
  - iv. a bearing disposed between said impeller shaft and said irrigation tube;
- a handpiece having an interior space into which a proximal portion of said elongate probe extends;
- a drive assembly for rotating the impeller shaft;
- an irrigation channel disposed in said handpiece interior space, said irrigation channel being in fluid communication with an annular space formed in said elongate probe between said irrigation tube and said impeller shaft; and
- an aspiration channel disposed in said handpiece interior space, said aspiration channel being in fluid communication with the lumen of said impeller shaft.

26. The device of claim 25 wherein the drive assembly is disposed in said handpiece interior space and is connected to a proximal portion of said impeller shaft such that said impeller shaft rotates upon operation of said drive assembly; and
- a translation apparatus at least partially disposed in said handpiece interior space and connected to longitudinally displace said drive assembly.

27. The device of claim 26 wherein said drive assembly is pneumatic and comprises a turbine, wherein a direct drive connection transfers rotational energy from said turbine to said impeller shaft.

28. The device of claim 26 wherein said translation apparatus comprises an inflatable bladder disposed between said handpiece back end and said drive assembly.

29. The device of claim 28 wherein said device includes a spring to bias the drive assembly to retract to a position proximate the back end of said handpiece when said bladder is not inflated.

30. The device of claim 26 wherein said irrigation channel includes a tube projecting from said handpiece back end and connected to translate with said drive assembly, the tube being connectable to a fluid supply tube.

31. The device of claim 30 further including a fitting on the tube that fits within a stepped recess in the handpiece back end, and a spring between the fitting and stepped recess to bias the fitting in a proximal direction.

32. The device of claim 26 wherein said aspiration channel includes a tube projecting from said handpiece back end and connected to translate with said drive assembly, the tube being connectable to a source of negative pressure.

33. The device of claim 32 further including a fitting on the tube that fits within a stepped recess in the handpiece back end, and a spring between the fitting and stepped recess to bias the fitting in a proximal direction.

34. A medical device comprising:
- an elongate probe insertable into a body and defining a longitudinal axis, said probe comprising a hollow impeller shaft defining a lumen and having a tool disposed at a distal end of said shaft, wherein an axis of rotation of said tool is generally coincident with said longitudinal axis;
- a handpiece having an interior space and a front end, wherein a proximal portion of said elongate probe extends through said front end and into said handpiece interior space;
- a drive assembly disposed in said handpiece interior space, said drive assembly being connected to a proximal portion of said impeller shaft such that said impeller shaft rotates upon operation of said drive assembly;
- an irrigation channel disposed in said handpiece interior space, said irrigation channel being in fluid communication with an irrigation conduit formed in said elongate probe;
- an aspiration channel disposed in said handpiece interior space, and aspiration channel being in fluid communication with the lumen of said impeller shaft; and
- a fluid block about the impeller shaft between said drive assembly and said handpiece front end, the fluid block providing a barrier between the irrigation channel and aspiration channel.

35. The device of claim 34, further comprising a translation apparatus for longitudinally moving said drive assembly, said translation apparatus being at least partially disposed in said handpiece interior space.

36. The device of claim 35, wherein said translation apparatus comprises an inflatable bladder disposed between a back end of said handpiece and said drive assembly.

37. The device of claim 36 further including a port extending through said handpiece back end and adapted for connecting a compressed gas source to said bladder interior to inflate said bladder.

38. The device of claim 37 wherein the fluid block also provides a barrier ft between both the irrigation channel and aspiration channel, and the compressed gas port.

39. The device of claim 34 wherein said elongate probe further comprises a tubular sheath comprising a mouth having an apex that extends beyond a distal end of said tool during operation thereby shielding a first side of said tool, wherein the mouth is angled so that a portion of said tool extends beyond a plane defined by the mouth, thus allowing the tool.

40. The device of claim 39 further comprising a translation apparatus for longitudinally moving said drive assembly, said translation apparatus being at least partially disposed in said handpiece interior space, wherein a proximal end of said tubular sheath is fixedly attached to the handpiece such that during longitudinal translation of said drive assembly, said sheath and said handpiece remain static relative to said drive assembly and said hollow shaft.

41. The device of claim 40, further comprising an irrigation tube within said tubular sheath that translates with said hollow shaft but is rotationally fixed with respect to the tubular sheath, and a bearing disposed between said hollow shaft and said irrigation tube.

42. The device of claim 34 wherein said tool comprises one or more blades, each of said blades comprising first and second portions, wherein said blade first portion extends approximately radially from said hollow shaft distal end and said blade second portion extends axially and distally from an outward edge of said blade first portion.

43. The device of claim 42, wherein said tool is formed integrally with said hollow shaft.

* * * * *